United States Patent
Nguyen et al.

(10) Patent No.: US 12,313,772 B2
(45) Date of Patent: May 27, 2025

(54) JOINT ESTIMATION OF RESPIRATORY AND HEART RATES USING ULTRA-WIDEBAND RADAR

(71) Applicant: Samsung Electronics Co., Ltd., Suwon-si (KR)

(72) Inventors: Hoang Viet Nguyen, Plano, TX (US); Raghunandan M. Rao, Allen, TX (US); Yuming Zhu, Plano, TX (US); Yi Yang, Suwon-si (KR); Jiho Shin, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 333 days.

(21) Appl. No.: 17/664,200

(22) Filed: May 19, 2022

(65) Prior Publication Data
US 2022/0373646 A1    Nov. 24, 2022

Related U.S. Application Data

(60) Provisional application No. 63/302,734, filed on Jan. 25, 2022, provisional application No. 63/191,638, filed on May 21, 2021.

(51) Int. Cl.
*G01S 7/41* (2006.01)
*A61B 5/0205* (2006.01)
*G01S 13/88* (2006.01)

(52) U.S. Cl.
CPC .......... *G01S 7/414* (2013.01); *A61B 5/0205* (2013.01); *G01S 13/88* (2013.01)

(58) Field of Classification Search
CPC ........ G01S 7/414; G01S 13/88; A61B 5/0205
USPC ...................................................... 342/28
See application file for complete search history.

(56) References Cited

U.S. PATENT DOCUMENTS

| 10,401,479 B2 | 9/2019 | Mabrouk et al. |
| 2008/0074307 A1 | 3/2008 | Boric-Lubecke et al. |

(Continued)

FOREIGN PATENT DOCUMENTS

| CN | 110507293 A | 11/2019 |
| CN | 113435283 A | 9/2021 |
| CN | 113729655 A | 12/2021 |
| KR | 101836761 B1 | 3/2018 |
| KR | 101895324 B1 | 9/2018 |

OTHER PUBLICATIONS

Khan et al, "An Overview of Signal Processing Techniques for Remote Health Monitoring Using Impulse Radio UWB Transceiver," Sensors 2020, 20, 2479; doi: 10.3390/s20092479 (Year: 2020).*

(Continued)

*Primary Examiner* — James R Hulka
*Assistant Examiner* — Samarina Makhdoom

(57) ABSTRACT

A method for contactless vital sign monitoring includes transmitting, via a transceiver, radar signals for object detection. The method also includes generating a clutter removed channel impulse response from received reflections of the radar signals a portion of which are reflected off of a living object. The method further includes identifying a set of range bins corresponding to a position of the living object. Additionally, the method includes identifying a first set of signal components representing a respiration rate of the living object and a second set of signal components representing a heart rate of the living object.

20 Claims, 17 Drawing Sheets

(56) References Cited

U.S. PATENT DOCUMENTS

| | | | | |
|---|---|---|---|---|
| 2015/0054670 | A1* | 2/2015 | Wang | A61B 5/0816 |
| | | | | 342/21 |
| 2015/0112220 | A1* | 4/2015 | Sana | A61B 5/05 |
| | | | | 600/534 |
| 2018/0333103 | A1* | 11/2018 | Bardan | A61B 5/0002 |
| 2019/0142289 | A1 | 5/2019 | Bliss et al. | |
| 2019/0166030 | A1* | 5/2019 | Chen | H04L 7/042 |
| 2019/0336038 | A1* | 11/2019 | Gorgutsa | A61B 5/0816 |
| 2020/0278438 | A1 | 9/2020 | Huang et al. | |
| 2020/0300972 | A1* | 9/2020 | Wang | A61B 5/0002 |
| 2020/0367810 | A1* | 11/2020 | Shouldice | H04R 1/08 |
| 2021/0401296 | A1 | 12/2021 | Chowdhury et al. | |

OTHER PUBLICATIONS

International Search Report and Written Opinion issued Sep. 13, 2022 regarding International Application No. PCT/KR2022/007279, 9 pages.

Lopes, "Bio-Radar Applications for Remote Vital Signs Monitoring", Master Thesis, NOVA University of Lisbon, Nov. 2020, 161 pages.

Wang et al., "Experimental Comparison of IR-UWB Radar and FMCW Radar for Vital Signs", Sensors, Nov. 2020, vol. 20, No. 22, 22 pages.

Dragomiretskiy, et al., "Variational Mode Decomposition", IEEE Transactions on Signal Processing, vol. 62, No. 3, Feb. 1, 2014, 14 pages.

Extended European Search Report issued May 8, 2024 regarding Application No. 22805042.3, 11 pages.

Shen et al., "Respiration and Heartbeat Rates Measurement Based on Autocorrelation Using IR-UWB Radar", IEEE Transactions on Circuits and Systems—II: Express Briefs, vol. 65, No. 10, Oct. 2018, pp. 1470-1474.

Baldi et al., "Analysis and Simulation of Algorithms for Vital Signs Detection Using UWB Radars", 2011 IEEE International Conference on Ultra-Wideband (ICUWB), Sep. 2011, pp. 341-345.

European Patent Office, Communication pursuant to Article 94(3) EPC issued Dec. 18, 2024 regarding Application No. 22805042.3, 5 pages.

\* cited by examiner

JOINT ESTIMATION OF RESPIRATORY AND HEART RATES USING ULTRA-WIDEBAND RADAR

CROSS-REFERENCE TO RELATED APPLICATION AND CLAIM OF PRIORITY

This application claims priority under 35 U.S.C. § 119(e) to U.S. Provisional Patent Application No. 63/191,638 filed on May 21, 2021, and U.S. Provisional Patent Application No. 63/302,734 filed on Jan. 25, 2022. The above-identified provisional patent applications are hereby incorporated by reference in their entirety.

TECHNICAL FIELD

This disclosure relates generally to vital monitoring. More specifically, this disclosure relates to joint estimation of respiratory and heart rates using radar.

BACKGROUND

Vital monitoring, such as heart rate, respiratory rate and the like, provide an easy way to gauge the health of a person. Additional insight into the health of a person can be gained by measuring vitals during different activities, such as when the person is exercising, sleeping, or relaxing. For example, heart rate and/or respiration rate an individual can provide an understanding as to the fitness level of the individual, ongoing pathological conditions of the individual, heart health of the individual, emotional health of the individual, and the like. Heart rate is the number of times the heart beats within a certain time period. Similarly, a respiration rate is the number of breaths a person breathes within a certain time period.

Various devices can be used to measure the heart and respiratory rates. However, such devices typically require direct contact with the user. For example, a pulse oximeter is a device that requires physical contact with a person to measure an individual's oxygen saturation, and pulse. However, oxygen saturation does not directly correlate to a respiratory rate of an individual and the corresponding overall health of that individual. Since the devices which can measure heart and respiratory rates require direct contract with a human body, the contact can cause discomfort to the individual and may not be suitable for prolonged monitoring (such as while sleeping or exercising). The ability to measure vitals in a contactless environment can improve comfort and overall health of an individual.

SUMMARY

This disclosure provides joint estimation of respiratory and heart rates using radar.

In one embodiment, electronic device is provided. The electronic device includes a transceiver and a processor. The processor is operably connected to the transceiver. The processor is configured to transmit, via the transceiver, radar signals for object detection. The processor is also configured to generate a clutter removed channel impulse response (CIR) from received reflections of the radar signals a portion of which are reflected off of a living object. The processor further configured to identify a set of range bins corresponding to a position of the living object based in part on the clutter removed CIR. Additionally, the processor is configured to identify a first set of signal components representing a respiration rate of the living object and a second set of signal components representing a heart rate of the living object. To identify the first set of signal components and the second set of signal components, the processor is configured to (i) in a first operation, identify the first set of signal components and the second set of signal components using variational mode decomposition (VMD) that decomposes a non-stationary signal of the set of range bins into subcomponents representing the respiration rate and the heart rate, or (ii) in a second operation, identify the first set of signal components from a generated frequency spectrum and identify the second set of signal components based on properties of a generated power spectrum density using the set of range bins.

In another embodiment, a method is provided. The method includes transmitting, via a transceiver, radar signals for object detection. The method also includes generating a clutter removed CIR from received reflections of the radar signals a portion of which are reflected off of a living object. The method further includes identifying a set of range bins corresponding to a position of the living object based in part on the clutter removed CIR. Additionally, the method includes identifying a first set of signal components representing a respiration rate of the living object and a second set of signal components representing a heart rate of the living object. Identifying the first set of signal components and the second set of signal components the method includes (i) identifying the first set of signal components and the second set of signal components using VMD that decomposes a non-stationary signal of the set of range bins into subcomponents representing the respiration rate and the heart rate, or (ii) identifying the first set of signal components from a generated frequency spectrum and identify the second set of signal components based on properties of a generated power spectrum density using the set of range bins.

In yet another embodiment a non-transitory computer-readable medium embodying a computer program, the computer program comprising computer readable program code that, when executed by a processor of an electronic device, causes the processor to: transmit, via a transceiver, radar signals for object detection; generate a clutter removed CIR from received reflections of the radar signals a portion of which are reflected off of a living object; identify a set of range bins corresponding to a position of the living object based in part on the clutter removed CIR; identify a first set of signal components representing a respiration rate of the living object and a second set of signal components representing a heart rate of the living object. To identify the first set of signal components and the second set of signal components, the computer program further comprises computer readable program code that, when executed by the processor, causes the processor to: identify the first set of signal components and the second set of signal components using VMD that decomposes a non-stationary signal of the set of range bins into subcomponents representing the respiration rate and the heart rate, or identify the first set of signal components from a generated frequency spectrum and identify the second set of signal components based on properties of a generated power spectrum density using the set of range bins.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
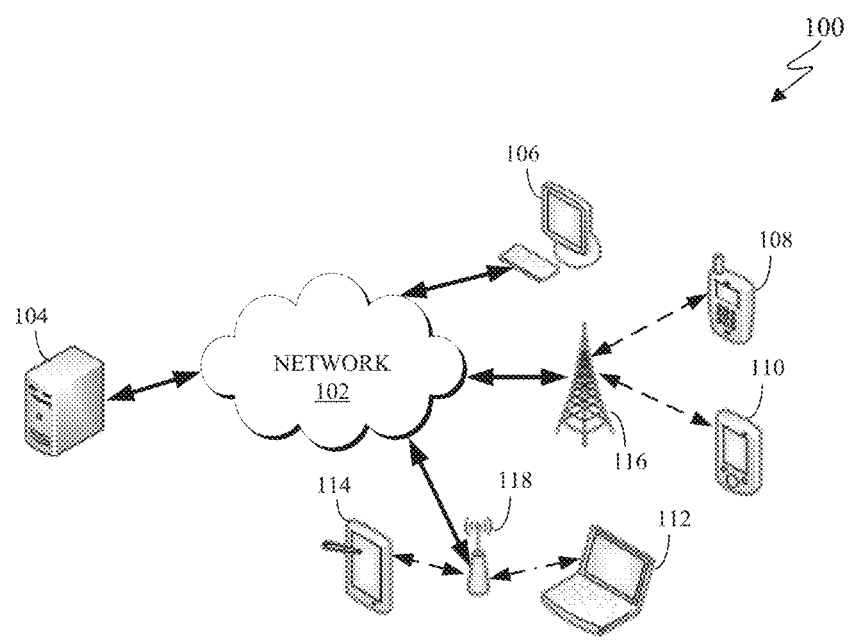
FIG. 1 illustrates an example communication system in accordance with an embodiment of this disclosure.

FIGS. 1 through 7, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

An electronic device, according to embodiments of the present disclosure can include a user equipment (UE) such as a 5G terminal. The electronic device can also refer to any component such as mobile station, subscriber station, remote terminal, wireless terminal, receive point, vehicle, or user device. The electronic device could be a mobile telephone, a smartphone, a monitoring device, an alarm device, a fleet management device, an asset tracking device, an automobile, a desktop computer, an entertainment device, an infotainment device, a vending machine, an electricity meter, a water meter, a gas meter, a security device, a sensor device, an appliance, and the like. Additionally, the electronic device can include a personal computer (such as a laptop, a desktop), a workstation, a server, a television, an appliance, and the like. In certain embodiments, an electronic device can be a portable electronic device such as a portable communication device (such as a smartphone or mobile phone), a laptop, a tablet, an electronic book reader (such as an e-reader), a personal digital assistants (PDAs), a portable multimedia player (PMP), an MP3 player, a mobile medical device, a virtual reality headset, a portable game console, a camera, and a wearable device, among others. Additionally, the electronic device can be at least one of a part of a piece of furniture or building/structure, an electronic board, an electronic signature receiving device, a projector, or a measurement device. The electronic device is one or a combination of the above-listed devices. Additionally, the electronic device as disclosed herein is not limited to the above-listed devices and can include new electronic devices depending on the development of technology. It is noted that as used herein, the term "user" may denote a human or another device (such as an artificial intelligent electronic device) using the electronic device.

Embodiments of the present disclosure recognize and take into consideration that radar technology is used in areas of commerce, defense and security. More recently, small, low cost and solid-state radar technologies have enabled civilian applications such as medical and automotive, enhanced human-machine interface, and smart interaction with environments. In certain embodiments, a radar system can transmit radar signals towards and one or more passive targets (or objects), which scatters signals incident on them. The radar monitors a region of interest (ROI) by transmitting signals and measures the environment's response to perform functions including but not limited to proximity sensing, vital sign detection, gesture detection, and target detection and tracking. Ultra-wideband (UWB) radar is an example radar signal type.

In certain embodiments, such as those described in FIG. 3 below, UWB radar includes a transceiver (or at least one radar transmitter and receiver). The transceiver can transmit a high-bandwidth pulse, receives the signal scattered from an object (also denoted as a target). The UWB radar or the electronic device can compute the channel impulse response (CIR), a signature of the target and its surroundings. The radar is equipped with one or more receive antennas ($RX_1$, $RX_2$, . . . , $RX_n$) to enable signal processing in time-frequency-space domains. The radar system can provide the targets' range, Doppler frequency, and spatial spectrum information for the time indices of interest.

Embodiments of the present disclosure take into consideration that vital signs of living object can be monitored using various devices. For example, certain devices may need to be in contact with the living object in order to detect heart rate or respiration rate. For another example, a camera-based approach can be used, providing a contact free approach for vital monitoring. However, poor lighting conditions can detrimentally affect the captured images for vital sign monitoring, causing inaccurate result. Additionally, a camera may be unable to detect heart rate of a user due to the negligible fluctuations of the surface (skin) user during each pulse.

Accordingly, embodiments of the present disclosure include systems and methods for using radar for contact free monitoring vitals of a user regardless of lighting conditions. For example, embodiments of the present disclosure describe using impulse radio ultra-wideband (IR-UWB) radar system to monitor vitals without direct contact of the individual in any lighting condition. In IR-UWB, amplitude variations and time of arrival (ToA) of the reflected pulses are used for evaluating breathing and heart rates of a subject.

In certain embodiments, an electronic device can transmit high bandwidth pulses of radar signals (such as IR-UWB signals) towards a subject whose vitals are to be monitored. The subject can be sitting in front of the radar and breaths normally. Some of the signals reflected off of the subject can be received by the electronic device. The reflected signals that bounce off of the chest of the subject can be used to identify a respiration rate and heart rate of that subject.

Embodiments of the present disclosure take into consideration that separation of heart rate from respiration rate is difficult as the signal corresponding to the heart rate is much weaker as compared to the signal corresponding to respiration. Additionally, embodiments of the present disclosure take into consideration that the signal corresponding to heart rate can be masked by the harmonics of the respiratory signal.

Accordingly, embodiments of the present disclosure describe methods and systems to jointly detect the respiratory rate and the heart rate from received radar signals. As described herein the radar signals are IR-UWB, however other types of radar signals can be used.

In certain embodiments, UWB radar is used to monitor respiratory rate and heart rate of a living object that is located in front of the radar. For example, a smart speaker can be located on the nightstand beside a person's bed. The smart speaker can include a UWB radar that is pointing toward the person while the person is sleeping. The smart speaker can monitor the breathing rate and heart rate of the person while the person is sleeping. This information can provide insight into sleep quality (e.g., length of restful periods, sleep apnea detection, etc.) of the person and also used to provide suggestion for better sleep.

For another example, a smart phone with UWB radar capabilities can be located in a charging stand that is located in front of a person while the person is working at their desk. The UWB radar embedded in the phone can detect the persons position and monitor their breathing rate and heart rate during the time they are working. The breathing rate and heart rate information can then be used for a daily summary of the persons stress level and used to provide a suggestion (such as a suggestion that the person take a temporary break to avoid tiredness.

For another example, an athlete/runner/sport player can pull out their phone (which has embedded UWB radar) and hold the device in front of them while training or working out. After a few seconds, the phone can report current breathing rate and heart rate of the user.

For yet another example, when a person is feeling the onset of a physiological anomaly (e.g., light-headed, chest pain, breathing difficulty, etc.), the user can pull out their phone, (which has embedded UWB radar) and place it in front of them. After a few seconds, the phone can accurately report current breathing rate and heart rate of the user, thus providing the user with an indication of the possibility of a medical emergency (such as cardiac arrest).

FIG. 1 illustrates an example communication system 100 in accordance with an embodiment of this disclosure. The embodiment of the communication system 100 shown in FIG. 1 is for illustration only. Other embodiments of the communication system 100 can be used without departing from the scope of this disclosure.

The communication system 100 includes a network 102 that facilitates communication between various components in the communication system 100. For example, the network 102 can communicate IP packets, frame relay frames, Asynchronous Transfer Mode (ATM) cells, or other information between network addresses. The network 102 includes one or more local area networks (LANs), metropolitan area networks (MANs), wide area networks (WANs), all or a portion of a global network such as the Internet, or any other communication system or systems at one or more locations.

In this example, the network 102 facilitates communications between a server 104 and various client devices 106-114. The client devices 106-114 may be, for example, a smartphone (such as a UE), a tablet computer, a laptop, a personal computer, a wearable device, a head mounted display, or the like. The server 104 can represent one or more servers. Each server 104 includes any suitable computing or processing device that can provide computing services for one or more client devices, such as the client devices 106-114. Each server 104 could, for example, include one or more processing devices, one or more memories storing instructions and data, and one or more network interfaces facilitating communication over the network 102.

Each of the client devices 106-114 represent any suitable computing or processing device that interacts with at least one server (such as the server 104) or other computing device(s) over the network 102. The client devices 106-114 include a desktop computer 106, a mobile telephone or mobile device 108 (such as a smartphone), a PDA 110, a laptop computer 112, and a tablet computer 114. However, any other or additional client devices could be used in the communication system 100, such as wearable devices. Smartphones represent a class of mobile devices 108 that are handheld devices with mobile operating systems and integrated mobile broadband cellular network connections for voice, short message service (SMS), and Internet data communications. In certain embodiments, any of the client devices 106-114 can emit and collect radar signals via a measuring (or radar) transceiver.

In this example, some client devices 108-114 communicate indirectly with the network 102. For example, the mobile device 108 and PDA 110 communicate via one or more base stations 116, such as cellular base stations or eNodeBs (eNBs) or gNodeBs (gNBs). Also, the laptop computer 112 and the tablet computer 114 communicate via one or more wireless access points 118, such as IEEE 802.11 wireless access points. Note that these are for illustration only and that each of the client devices 106-114 could communicate directly with the network 102 or indirectly with the network 102 via any suitable intermediate device(s) or network(s). In certain embodiments, any of the client devices 106-114 transmit information securely and efficiently to another device, such as, for example, the server 104.

In certain embodiments, any of the client devices 106-116 can emit and receive UWB signals via a measuring transceiver. For example, the mobile device 108 can transmit a UWB signal for vital detection and monitoring. Based on the received signals, the mobile device 108 can identify the heart rate and breathing rate of a subject whose vitals are to be monitored.

Although FIG. 1 illustrates one example of a communication system 100, various changes can be made to FIG. 1. For example, the communication system 100 could include any number of each component in any suitable arrangement. In general, computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

Figure 2:
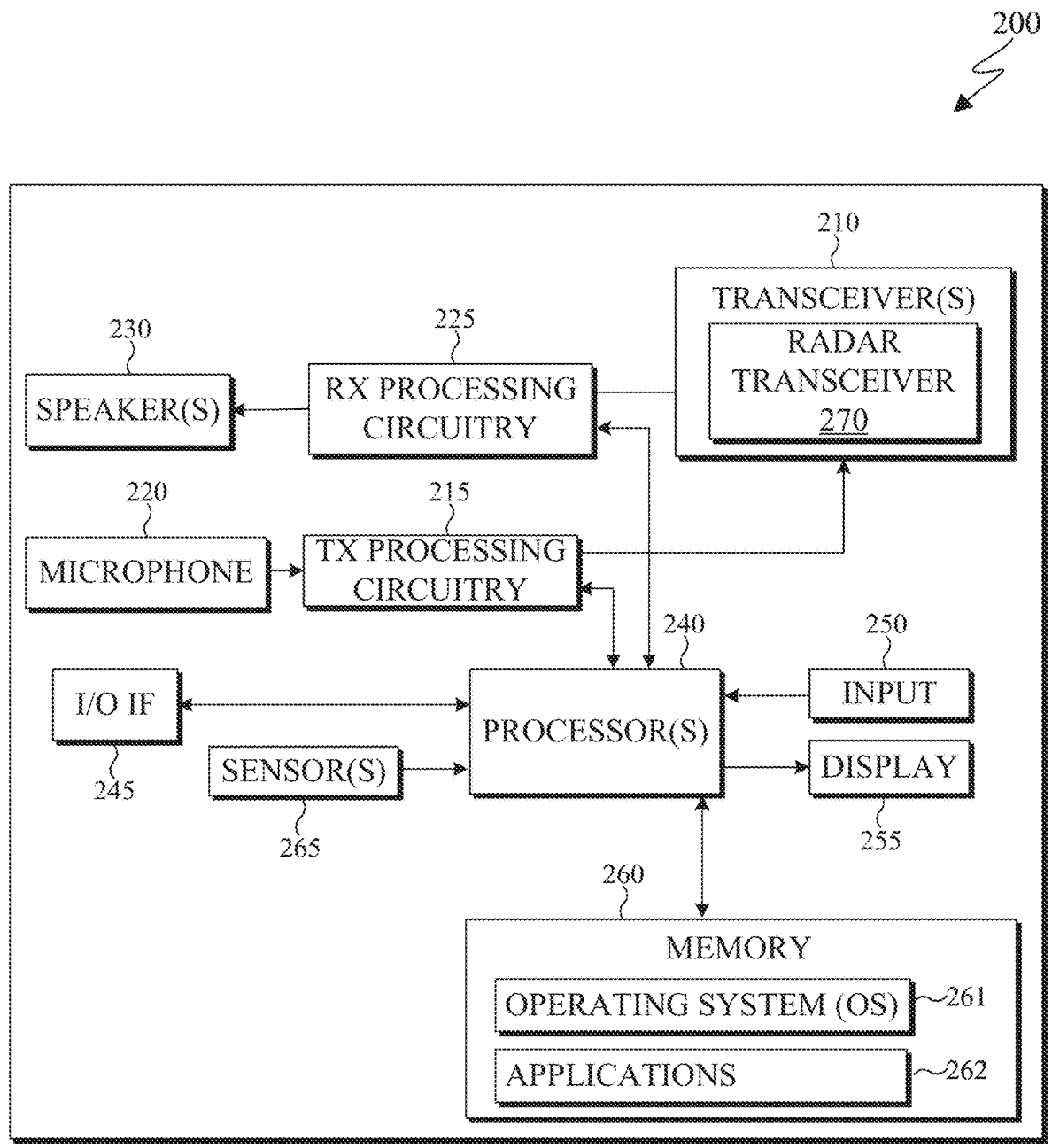
FIG. 2 illustrates an example electronic device in accordance with an embodiment of this disclosure.

FIG. 2 illustrates an example electronic device in accordance with an embodiment of this disclosure. In particular, FIG. 2 illustrates an example electronic device 200, and the electronic device 200 could represent the server 104 or one or more of the client devices 106-114 in FIG. 1. The electronic device 200 can be a mobile communication device, such as, for example, a UE, a mobile station, a subscriber station, a wireless terminal, a desktop computer (similar to the desktop computer 106 of FIG. 1), a portable electronic device (similar to the mobile device 108, the PDA 110, the laptop computer 112, or the tablet computer 114 of FIG. 1), a robot, and the like.

As shown in FIG. 2, the electronic device 200 includes transceiver(s) 210, transmit (TX) processing circuitry 215, a microphone 220, and receive (RX) processing circuitry 225. The transceiver(s) 210 can include, for example, a radio frequency (RF) transceiver, a BLUETOOTH transceiver, a WiFi transceiver, a ZIGBEE transceiver, an infrared transceiver, and various other wireless communication signals. The electronic device 200 also includes a speaker 230, a processor 240, an input/output (I/O) interface (IF) 245, an input 250, a display 255, a memory 260, and a sensor 265. The memory 260 includes an operating system (OS) 261, and one or more applications 262.

The transceiver(s) 210 can include an antenna array including numerous antennas. For example, the transceiver(s) 210 can be equipped with multiple antenna elements. There can also be one or more antenna modules fitted on the terminal where each module can have one or more antenna elements. The antennas of the antenna array can include a radiating element composed of a conductive material or a conductive pattern formed in or on a substrate. As illustrated, the transceiver 210 also includes a radar transceiver 270. The radar transceiver 270 is discussed in greater detail below.

The transceiver(s) 210 transmit and receive a signal or power to or from the electronic device 200. The transceiver(s) 210 receives an incoming signal transmitted from an access point (such as a base station, WiFi router, or BLUETOOTH device) or other device of the network 102 (such as a WiFi, BLUETOOTH, cellular, 5G, LTE, LTE-A, WiMAX, or any other type of wireless network). The transceiver(s) 210 down-converts the incoming RF signal to generate an intermediate frequency or baseband signal. The intermediate frequency or baseband signal is sent to the RX processing circuitry 225 that generates a processed baseband signal by filtering, decoding, and/or digitizing the baseband or intermediate frequency signal. The RX processing circuitry 225 transmits the processed baseband signal to the speaker 230 (such as for voice data) or to the processor 240 for further processing (such as for web browsing data).

The TX processing circuitry 215 receives analog or digital voice data from the microphone 220 or other outgoing baseband data from the processor 240. The outgoing baseband data can include web data, e-mail, or interactive video game data. The TX processing circuitry 215 encodes, multiplexes, and/or digitizes the outgoing baseband data to generate a processed baseband or intermediate frequency signal. The transceiver(s) 210 receives the outgoing processed baseband or intermediate frequency signal from the TX processing circuitry 215 and up-converts the baseband or intermediate frequency signal to a signal that is transmitted.

The processor 240 can include one or more processors or other processing devices. The processor 240 can execute instructions that are stored in the memory 260, such as the OS 261 in order to control the overall operation of the electronic device 200. For example, the processor 240 could control the reception of forward channel signals and the transmission of reverse channel signals by the transceiver(s) 210, the RX processing circuitry 225, and the TX processing circuitry 215 in accordance with well-known principles. The processor 240 can include any suitable number(s) and type(s) of processors or other devices in any suitable arrangement. For example, in certain embodiments, the processor 240 includes at least one microprocessor or microcontroller. Example types of processor 240 include microprocessors, microcontrollers, digital signal processors, field programmable gate arrays, application specific integrated circuits, and discrete circuitry. In certain embodiments, the processor 240 can include a neural network.

The processor 240 is also capable of executing other processes and programs resident in the memory 260, such as operations that receive and store data. The processor 240 can move data into or out of the memory 260 as required by an executing process. In certain embodiments, the processor 240 is configured to execute the one or more applications 262 based on the OS 261 or in response to signals received from external source(s) or an operator. Example, applications 262 can include a multimedia player (such as a music player or a video player), a phone calling application, a virtual personal assistant, and the like.

The processor 240 is also coupled to the I/O interface 245 that provides the electronic device 200 with the ability to connect to other devices, such as client devices 106-114. The I/O interface 245 is the communication path between these accessories and the processor 240.

The processor 240 is also coupled to the input 250 and the display 255. The operator of the electronic device 200 can use the input 250 to enter data or inputs into the electronic device 200. The input 250 can be a keyboard, touchscreen, mouse, track ball, voice input, or other device capable of acting as a user interface to allow a user in interact with the electronic device 200. For example, the input 250 can include voice recognition processing, thereby allowing a user to input a voice command. In another example, the input 250 can include a touch panel, a (digital) pen sensor, a key, or an ultrasonic input device. The touch panel can recognize, for example, a touch input in at least one scheme, such as a capacitive scheme, a pressure sensitive scheme, an infrared scheme, or an ultrasonic scheme. The input 250 can be associated with the sensor(s) 265, the radar transceiver 270, a camera, and the like, which provide additional inputs to the processor 240. The input 250 can also include a control circuit. In the capacitive scheme, the input 250 can recognize touch or proximity.

The display 255 can be a liquid crystal display (LCD), light-emitting diode (LED) display, organic LED (OLED), active-matrix OLED (AMOLED), or other display capable of rendering text and/or graphics, such as from websites, videos, games, images, and the like. The display 255 can be a singular display screen or multiple display screens capable of creating a stereoscopic display. In certain embodiments, the display 255 is a heads-up display (HUD).

The memory 260 is coupled to the processor 240. Part of the memory 260 could include a RAM, and another part of the memory 260 could include a Flash memory or other ROM. The memory 260 can include persistent storage (not shown) that represents any structure(s) capable of storing and facilitating retrieval of information (such as data, program code, and/or other suitable information). The memory 260 can contain one or more components or devices supporting longer-term storage of data, such as a read only memory, hard drive, Flash memory, or optical disc.

The electronic device 200 further includes one or more sensors 265 that can meter a physical quantity or detect an activation state of the electronic device 200 and convert metered or detected information into an electrical signal. For example, the sensor 265 can include one or more buttons for touch input, a camera, a gesture sensor, optical sensors, cameras, one or more inertial measurement units (IMUs), such as a gyroscope or gyro sensor, and an accelerometer. The sensor 265 can also include an air pressure sensor, a magnetic sensor or magnetometer, a grip sensor, a proximity sensor, an ambient light sensor, a bio-physical sensor, a temperature/humidity sensor, an illumination sensor, an Ultraviolet (UV) sensor, an Electromyography (EMG) sensor, an Electroencephalogram (EEG) sensor, an Electrocardiogram (ECG) sensor, an IR sensor, an ultrasound sensor, an iris sensor, a fingerprint sensor, a color sensor (such as a Red Green Blue (RGB) sensor), and the like. The sensor 265 can further include control circuits for controlling any of the sensors included therein. Any of these sensor(s) 265 may be located within the electronic device 200 or within a secondary device operably connected to the electronic device 200.

In this embodiment, one of the one or more transceivers in the transceiver 210 is a radar transceiver 270 that is configured to transmit and receive signals for detecting and ranging purposes. In certain embodiments, the radar transceiver 270 is a UWB radar transceiver. The radar transceiver 270 can transmit and receive signals for measuring range and speed of an object that is external to the electronic device 200. The radar transceiver 270 can also transmit and receive signals for measuring the angle a detected object relative to the electronic device 200. For example, the radar transceiver 270 can transmit one or more signals that when reflected off of a moving object and received by the radar transceiver 270 can be used for determining the range (distance between the object and the electronic device 200), the speed of the object, the angle (angle between the object and the electronic device 200), or any combination thereof. Using the received signals that are reflected off of a person, the electronic device 200 can determine a breathing rate and heart rate of the person.

The radar transceiver 270 may be any type of transceiver including, but not limited to a WiFi transceiver, for example, an 802.11ay transceiver, a UWB transceiver, and the like. The radar transceiver 270 can transmit signals at a various frequencies, such as in UWB. The radar transceiver 270 can receive the signals from an external electronic device as well as signals that were originally transmitted by the electronic device 300 and reflected off of an object external to the electronic device.

The radar transceiver 270 may be any type of transceiver including, but not limited to a radar transceiver. The radar transceiver 270 can include a radar sensor. The radar transceiver 270 can receive the signals, which were originally transmitted from the radar transceiver 270, after the signals have bounced or reflected off of target objects in the surrounding environment of the electronic device 200. In certain embodiments, the radar transceiver 270 is a monostatic radar as the transmitter of the radar signal and the receiver, for the delayed echo, are positioned at the same or similar location. For example, the transmitter and the receiver can use the same antenna or nearly co-located while using separate, but adjacent antennas. Monostatic radars are assumed coherent, such as when the transmitter and receiver are synchronized via a common time reference.

The processor 240 can analyze the time difference, based on the time stamps of transmitted and received signals, to measure the distance of the target objects from the electronic device 200. Based on the time differences, the processor 240 can generate location information, indicating a distance that the external electronic device is from the electronic device 200. In certain embodiments, the radar transceiver 270 is a sensor that can detect range and AOA of another electronic device. For example, the radar transceiver 270 can identify changes in azimuth and/or elevation of the external object relative to the radar transceiver 270.

Although FIG. 2 illustrates one example of electronic device 200, various changes can be made to FIG. 2. For example, various components in FIG. 2 can be combined, further subdivided, or omitted and additional components can be added according to particular needs. As a particular example, the processor 240 can be divided into multiple processors, such as one or more central processing units (CPUs), one or more graphics processing units (GPUs), one or more neural networks, and the like. Also, while FIG. 2 illustrates the electronic device 200 configured as a mobile telephone, tablet, or smartphone, the electronic device 200 can be configured to operate as other types of mobile or stationary devices.

Figure 3:
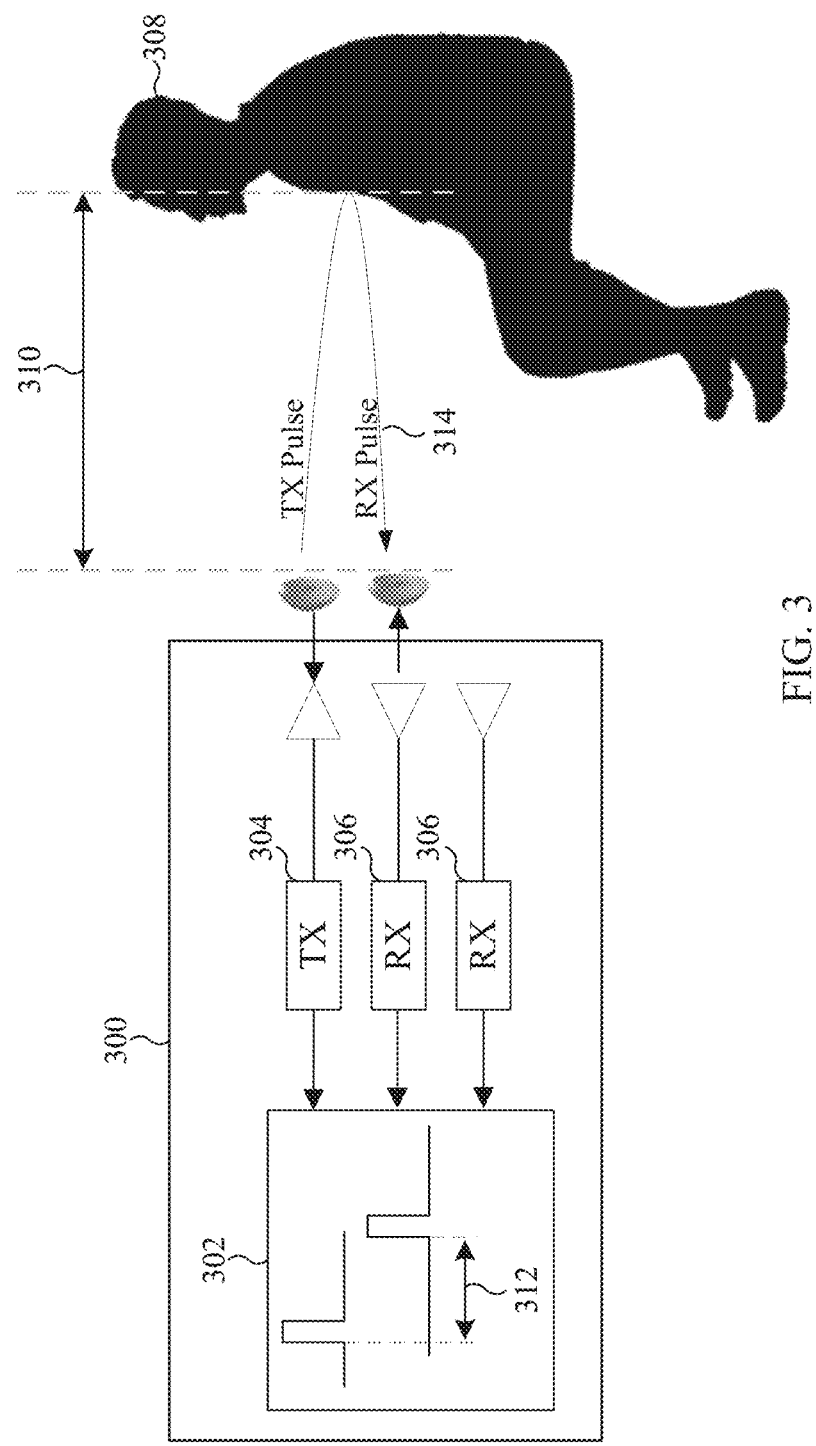
FIG. 3 illustrates an example architecture of an ultra-wideband (UWB) radar signal according to embodiments of this disclosure.

FIG. 3 illustrates an example architecture of a radar signal according to embodiments of this disclosure. The embodiments of FIG. 3 is for illustration only and other embodiments can be used without departing from the scope of the present disclosure.

FIG. 3 illustrates an electronic device 300 that includes a processor 302, a transmitter 304, and one or more receiver(s) 306. The electronic device 300 can be similar to any of the client devices 106-114 of FIG. 1, the server 104 of FIG. 1, or the electronic device 200 of FIG. 2. The processor 302 is similar to the processor 240 of FIG. 2. Additionally, the transmitter 304 and the receiver 306 can be included within the radar transceiver 270 of FIG. 2.

The transmitter 304 of the electronic device 300 transmits a signal 314 to the target object 308. The target object 308 is located a distance 310 from the electronic device 300. In certain embodiments, the target object 308 corresponds to an external object (such as a human or a human body part). For example, the target object 308 can be a living object (such as a human or animal) for which vital signs are to be monitored.

The transmitter 304 transmits a signal 314 via an antenna. The signal 314 is reflected off of the target object 308 and received by the receiver 306, via an antenna. The signal 314 represents one or many signals that can be transmitted from the transmitter 304 and reflected off of the target object 308. The processor 302 can identify the information associated with the target object 308, such as the speed the target object 308 is moving (including rate of repeated motions, such as breathing and heart beats) and the distance the target object 308 is from the electronic device 300, based on the receiver 306 receiving the multiple reflections of the signals, over a period of time.

Leakage (not shown) represents radar signals that are transmitted from the antenna associated with transmitter 304 and are directly received by the antenna associated with the receiver 306 without being reflected off of the target object 308.

In order to detect the target object 308, the processor 302 analyzes a time difference 312 from when the signal 314 is transmitted by the transmitter 304 and received by the receiver 306. It is noted that the time difference 312 is also referred to as a delay, as it indicates a delay between the transmitter 304 transmitting the signal 314 and the receiver 306 receiving the signal after the signal is reflected or bounced off of the target object 308. Based on the time difference 312, the processor 302 derives the distance 310 between the electronic device 300, and the target object 308. Additionally, based on multiple time differences 312 and changes in the distance 310, the processor 302 derives the speed that the target object 308 is moving.

For example, the electronic device 300 can transmit a high-bandwidth pulse, receive the signal reflected back from a target object 308, and computes the CIR. The CIR is a signature of the target object 308 and the surrounding environment. For example, if the target object 308 is a human subject, which is sitting in front of the radar and breaths normally as illustrated in FIG. 3, the signal bouncing back from the chest of the subject is then used to estimate the chest movement for determining respiratory and heart rates of the subject.

In IR-UWB, the amplitude variations as well as the ToA of the reflected pulse are used to evaluate the motions of the chest and heart, enabling the respiratory rate and heart rate can be derived. When a radar pulse is transmitted, the radar receives its echoes reflected from the subject. The distance 310 from the antenna to the target object 308 is described in Equation (1), below. In Equation (1), $d_0$ is the nominal distance between antenna and the human chest wall, $d_r$ is the displacement amplitude caused by respiration, $d_h$ is the displacement amplitude caused by heartbeat, $f_r$ represents the respiration frequency, and $f_h$ represents the heartbeat frequency, respectively.

$$s(t)=d_0+d(t)=d_0+d_r\sin(2\pi f_r t)+d_h\sin(2\pi f_h t) \quad (1)$$

The normalized received pulse, denoted by $\delta(t)$, and the total impulse response is described in Equation (2), below. In Equation (2), t is the observation time and $\tau$ is the propagation time. The expression $A_k\,\delta(\tau-\tau_k(t))$ denotes the response due to chest wall micro-motion with propagation time $\tau_k(t)$ and amplitude $A_k$. The expression $\Sigma_i A_i\delta(\tau-\tau_i)$ denotes the response from all multipath components, with $A_i$ being the amplitude of the $i^{th}$ multipath component, and $\tau_i$ being the propagation time of the $i^{th}$ multipath component.

$$r(t,\tau)=A_k\,\delta(\tau-\tau_k(t))+\Sigma_i A_i\delta(\tau-\tau_i) \quad (2)$$

The propagation time $\tau_k(t)$, of Equation (2), is determined by the antenna distance s(t), and described in Equation (3), below. In equation (3), c is the speed of light (about $3\times10^8$ m/s), $\tau_0=2s_0/c$, $\tau_r=2d_r/c$ and $\tau_h=2d_h/c$.

$$\tau_k(t)=2s(t)/c=\tau_0+\tau_r\sin(2\pi f_r t)+\tau_h\sin(2\pi f_h t) \quad (3)$$

In certain embodiments, the firmware of the UWB radar samples the continuous-time total impulse response $r(t,\tau)$ and generates a two-dimensional (2D) n×m matrix, denoted by h[n, m], as described in Equation (4), below. In Equation (4), the expressions n and m represent the sampling numbers in slow time and fast time, respectively. Additionally, the expressions $T_s$ of Equation (4) is the pulse duration in slow time, and the expression $T_f$ of Equation (4) is the fast time sampling interval. Hence, the row vectors record the received signals at different observation times at each range bin while the column vectors record one pulse reflected from different range bins.

$$h[n,m]=r(t=nT_s,\tau=mT_f) \quad (4)$$

Accordingly, as used herein raw CIR, is described in Equation (5), below. As described in Equation (5), the raw CIR h[n,m] is for by for the $n^{th}$ slow time index and $m^{th}$ range bin on the RX antenna, where $N_r$ is the number of range bins. The variations in the CIR can be used to evaluate the motions of the chest and heart, then the respiratory rate and heart rate can be derived.

$$h[n,m](m=1,2,\ldots,N_r) \quad (5)$$

Although FIG. 3 illustrates electronic device 300 various changes can be made to FIG. 3. For example, different antenna configurations can be activated, different frame timing structures can be used or the like. FIG. 3 does not limit this disclosure to any particular radar system or apparatus.

Embodiments of the present disclosure take into consideration that separating heartbeat signals in the presence of respiratory signals is difficult since the heartbeat signal can be weak and/or masked by the harmonics of the respiratory signal in the frequency spectrum. Accordingly, embodiments of the present disclosure describe identifying heart rate and breathing rate using a variational mode decomposition (VMD), denoted as the first operation and described in FIGS. 4A-4D, as well as identifying the breathing rate and heart rate based on peak finding and classification, denoted as the second operation and described in FIGS. 5A-5H.

In the first operation, as described in FIGS. 4A-4D, the electronic device 200 applies clutter removal to raw CIR. The electronic device 200 then identifies the position of the subject (such as the target object 308 of FIG. 3) and selects relevant range bins surrounding the subject. A signal decomposition based on VMD is performed for each series of the relevant range bins. The electronic device 200 then identifies signal components including heartbeat and respiration signals based on intrinsic mode functions (IMFs).

In the second operation, as described in FIGS. 5A-5H, the electronic device 200 applies clutter removal to raw CIR. The clutter removal of the second operation is similar to the clutter removal of the first operation. The electronic device 200 can calculate a Chirp-Z transform (CZT) for each window of the clutter removed CIR. The electronic device 200 can then determine the position of the object and the breathing rate from the CZT map. Additionally, the electronic device 200 can also identify a power spectrum density (PSD) of each window of the clutter removed CIRs. The electronic device 200 determines the heart rate by finding peaks in the PSD and performs a classification. The electronic device 200 can also filter the heart rate to have to smoothen the results.

The final respiratory rate and heart rate are then provided to the user, such as by the display 255 of FIG. 2 or a speaker 230 of FIG. 2. The final respiratory and heart rates can be stored in the memory 260 of FIG. 2.

Figure 4A:
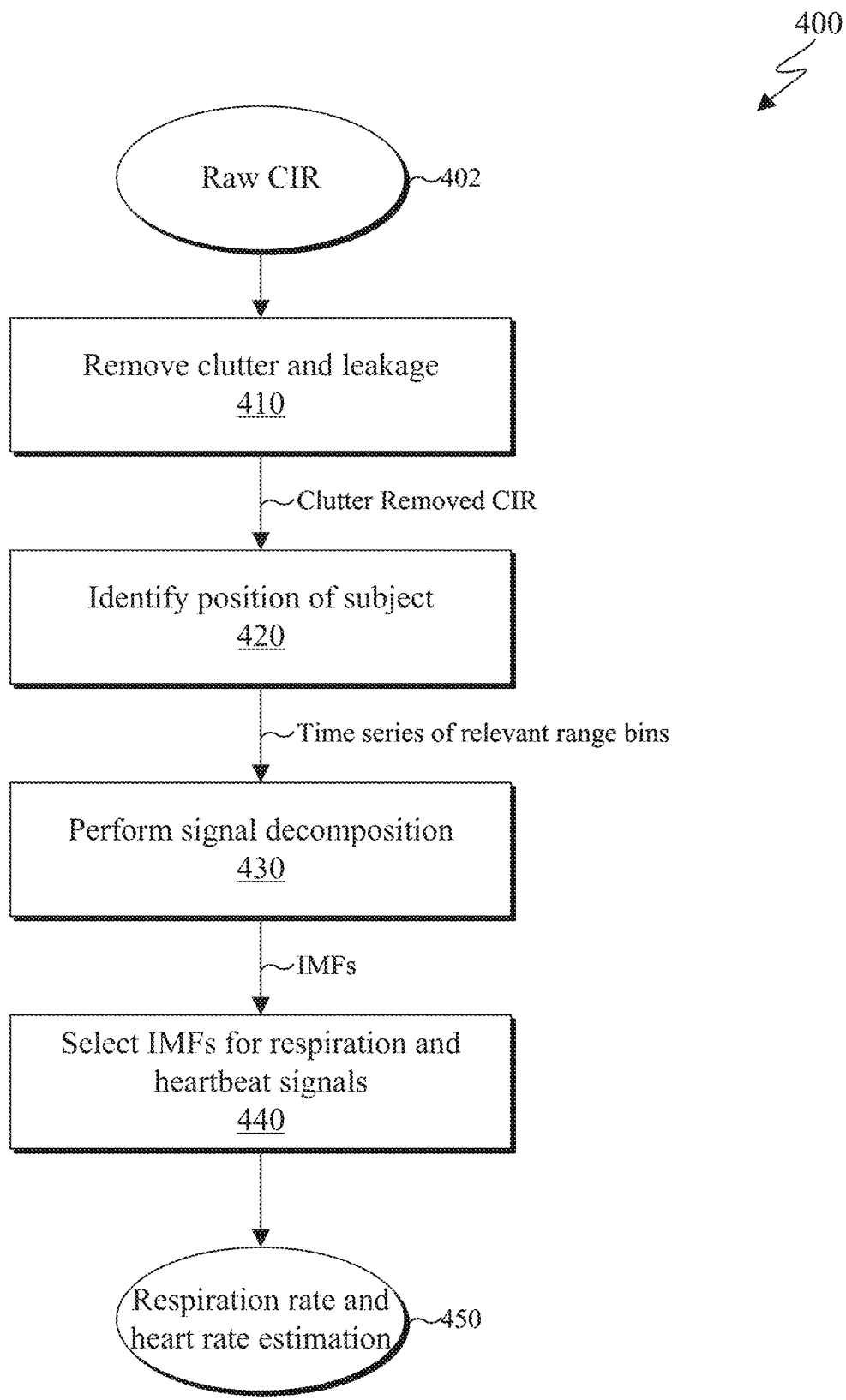
FIG. 4A illustrates an example method for vital monitoring according to embodiments of this disclosure.
Figure 4B:
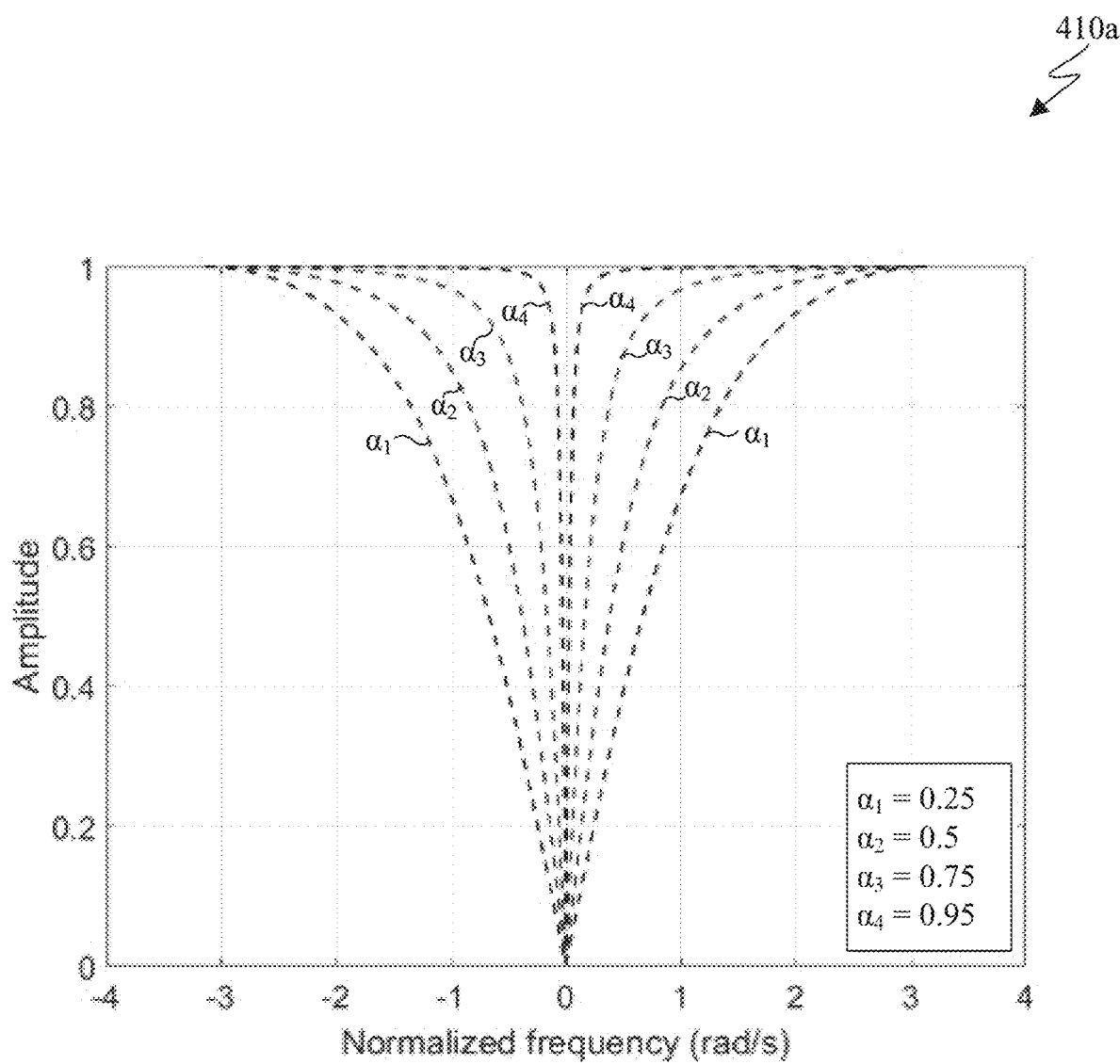
FIG. 4B illustrates an example of graph of a frequency response of a high-pass impulse response filter according to embodiments of this disclosure.
Figure 4C:
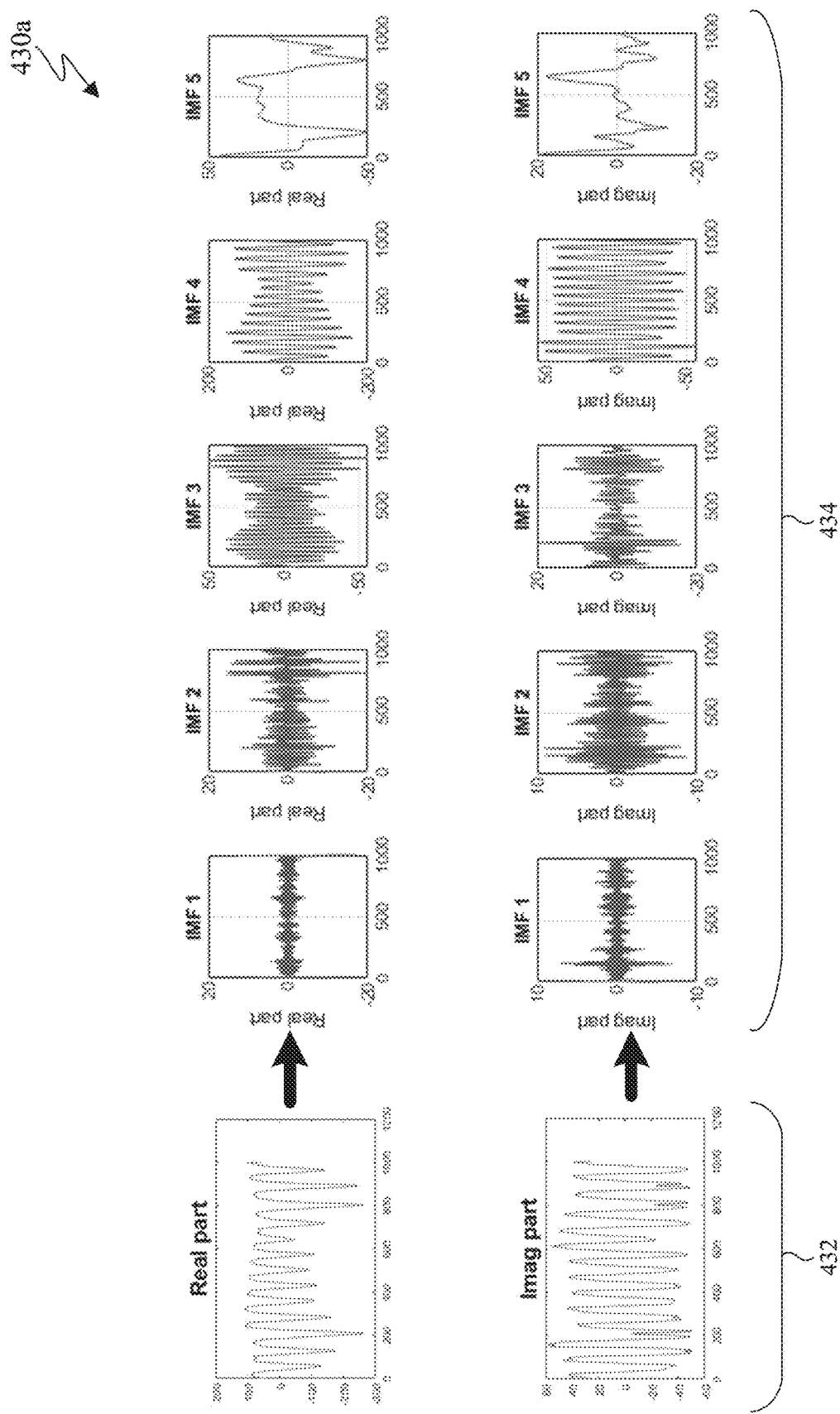
FIG. 4C illustrates an example diagram of decomposing real and imaginary parts of a range bin's channel impulse response (CIR) into intrinsic mode functions (IMFs) according to embodiments of this disclosure.
Figure 4D:
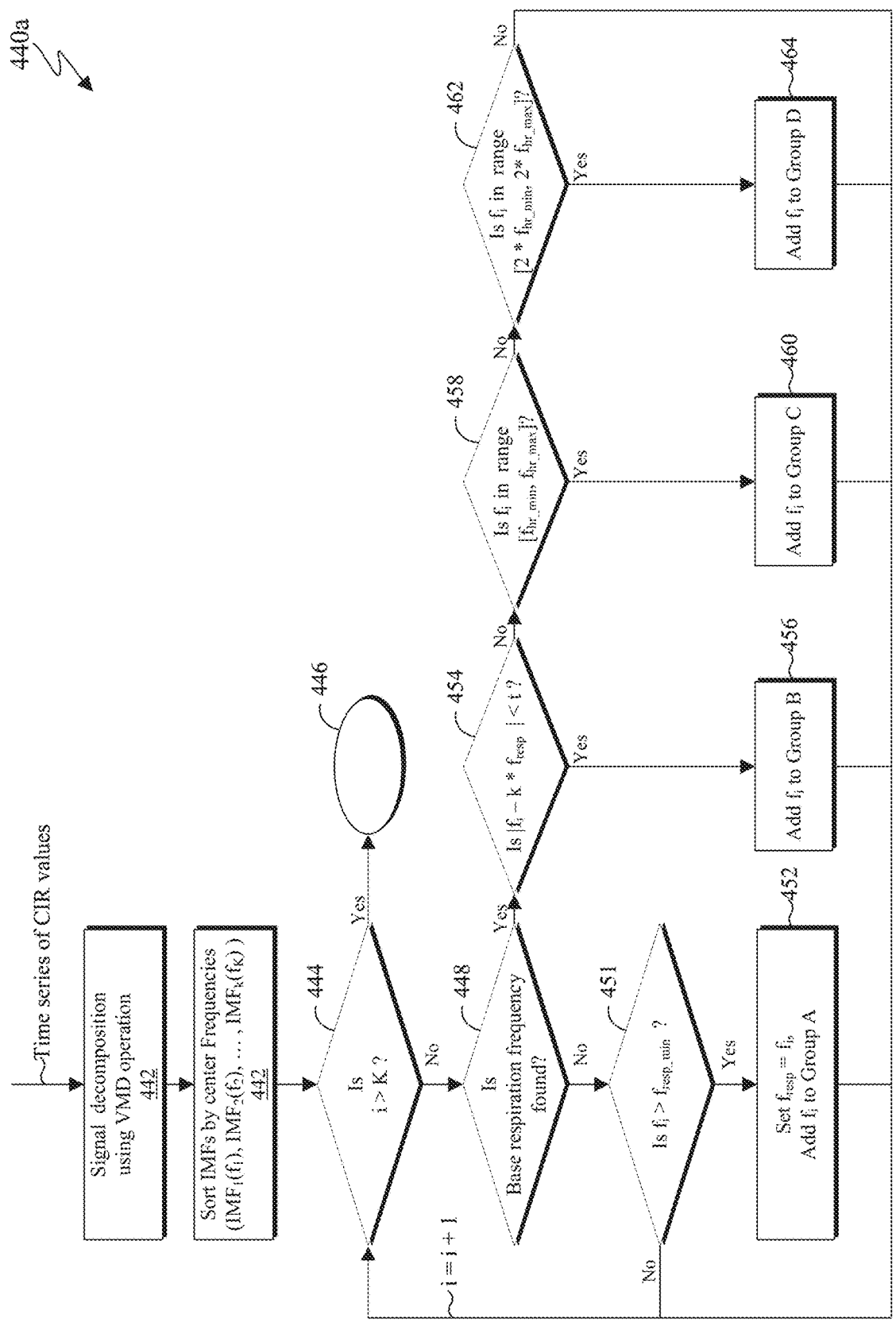
FIG. 4D illustrates an example method for classifying the IMFs into different groups according to embodiments of this disclosure.

FIG. 4A illustrates an example method 400 for vital monitoring according to embodiments of this disclosure. FIG. 4B illustrates an example of graph 410a of a frequency response of a high-pass impulse response filter according to embodiments of this disclosure. FIG. 4C illustrates an example diagram 430a of decomposing real and imaginary parts of a range bin's channel impulse response (CIR) into intrinsic mode functions (IMFs) according to embodiments of this disclosure. FIG. 4D illustrates an example method 440a for classifying the IMFs into different groups according to embodiments of this disclosure. The embodiments of FIGS. 4A-4D are for illustration only and other embodiments can be used without departing from the scope of the present disclosure.

The method 400 as illustrated in FIG. 4A and the method 440a as illustrated in FIG. 4D are described as implemented by any one of the client device 106-114 of FIG. 1, the server 104 of FIG. 1, the electronic device 300 of FIG. 3, and can include internal components similar to that of electronic device 200 of FIG. 2. However, 400 as shown in FIG. 4A and the method 440a as shown in FIG. 4D could be used with any other suitable electronic device and in any suitable system, such as when performed by the electronic device 200. For ease of explanation, the methods of FIGS. 4A and 4D are described as being performed by the electronic device 200 of FIG. 2.

The method 400, as illustrated in FIG. 4A, describes using a VMD process and a classification process to determine the type of each resulting decomposed function, whether it is respiration base frequency, respiration harmonics, heart rate base frequency or heart rate harmonics. It is noted that the method 400 assumes little body movement while big body movements can be easily detected by setting threshold on CIR energy level after clutter removal or using machine learning-based classifiers.

In step 410, the electronic device 200 removes clutter and leakage from received raw CIR 402. The raw CIR 402 can be IR-UW radar signals which are reflections of a transmitted pulses. The raw CIR 402 can include signals transmitted from the radar transmitter that reflected off of the chest a subject as well as signals that bounced back from the environment around the electronic device 200.

Since slow moving targets in the environment manifest as low-Doppler/low-frequency components in the CIR, in step 410, the electronic device 200 uses a high-pass filter for filtering out reflections of the UWB pulse due to static or very slow-moving objects. The chest movement results in breathing and heart rate signals being placed in the high frequency region of the received signal (the raw CIR 402). Thus, a high-pass filter, where low frequency components (typically caused by clutter) are discarded, can help extract the signal of interest for subsequent processing steps. For example, a high-pass infinite impulse response (IIR) filter can be used to suppress the clutter components. Equation (6) describes how to calculate clutter and Equation (7) describes the clutter removed CIR.

$$c[n,m]=ac[n-1,m]+(1-a)h[n,m] \quad (6)$$

$$h_c[n,m]=h[n,m]-c[n,m] \quad (7)$$

In the time domain, the clutter-removed CIR $h_c$ can be calculated described in Equation (6), above. In Equation (6), the parameter a is the clutter filter parameter, which controls the high-pass filter response. The parameter a is within the range from 0 to 1. FIG. 4B illustrates the graph 410a describing a frequency response of the high-pass IIR filter corresponding to different a parameter. The higher the parameter a is, the lower cut-off frequency of the high-pass filter is. Since breathing rate is typically in the range of 6-60 beat-per-minute (bpm) and heart rate is typically in the range of 48-200 bpm, a good cutoff frequency for the high-pass filter is 10 bpm (0.0167 Hz, or 0.1 rad/s). However other high-pass frequency cut offs can be used. As a result, a good range of the parameter a for breathing/heart rate estimation would be 0.95 to 1. It is noted that the parameter a is not limited thereto and can be other values as well.

Based on the parameter a, most of the static clutter is removed and only small movements, including chest movements caused by breathing and heart rate are maintained in the CIR.

In step 420, the electronic device 200 identifies the position of the subject using the clutter removed CIR (of step 410). If the subject is relatively still and the environment around the electronic device 200 is relatively motionless, the most significant movement in front of the measuring transceiver 270 of FIG. 2 is the motion of the chest of the subject as the subject inhales and exhales.

In certain embodiments, the electronic device 200 determines the position of the subject by comparing a standard deviation values of time series corresponding to the range bins. From a window of clutter-removed CIR (number of slow-time samples=N), for the time series of the $m^{th}$ range bin, its standard deviation is described in Equation (8), below.

$$s_m=std_{n=1}^N(|h_c[n,m]|^2) \quad (8)$$

The electronic device 200 then selects the range bin with maximum standard deviation value ($s_m$) as range bin corresponding to the subject. It is noted that this is based on an assumption that the most significant movement in front of the radar is the subject's chest movement, thus the range bin with the maximum standard deviation (largest movements) would likely be where the subject is. One or more range bins starting from the identified range with the highest standard deviation value ($s_m$) can be used to find the breathing rate and heart rate of the subject.

In certain embodiments, the electronic device 200 determines the position of the subject by comparing the total energy calculated from time series corresponding to the range bins. From a window of clutter-removed CIR (number of slow-time samples=N), for the time series of the $m^{th}$ range bin, its total energy is described in Equation (9), below.

$$e_m = \Sigma_{n=1}^{N}(|h_c[n,m]|^2) \qquad (9)$$

The electronic device 200 then selects the range bin with maximum of power value ($e_m$) as range bin where the subject is. It is noted that this is based on an assumption that the most significant movement in front of the radar is the subject's chest movement, thus the range bin with the maximum total energy (largest movements) would likely be where the subject is. One or more range bins starting from the identified range with the highest power value ($e_m$) can be used to find the breathing rate and heart rate of the subject.

It is noted that the above the examples (using a maximum standard deviation value ($s_m$) and a maximum of power value ($e_m$)) use energy-based detection to determine where the subject is. However, other methods, such as frequency-based methods for identifying the location of the subject can also be used. For example, the electronic device 200 can calculate the frequency spectrum from current CIR window. For another example, the electronic device 200 can identify on the frequency spectrum map the cell with frequency belongs to the breathing rate range (0.1-1 Hz), and Signal-to-Interference-and-noise ratio (SINR) higher than some threshold. The range bin corresponding to this cell can indicate where the target is located.

The range bin selected by the above methods would likely be where the chest of the subject is, as this location will the largest movements on the target object. The heart rate signal can be at a later range bin, due to the longer distance from the heart to the radar compared to from the chest to the radar. It can also appear in several later range bins, due to other reflection paths. Therefore, in certain embodiments, multiple range bins starting from the range bin found by the above-mentioned methods are considered to maximize the chance the heart rate signal can be found. The number of range bins for consideration depends on the range bin resolution of the UWB radar. In some embodiments, the multiple range bins can be about 1-3 range bins on either side of the range bin found (e.g., ±1 bin around range bin found, ±2 bins around range bin found, or ±3 bins around range bin found).

In step 430, the electronic device 200 a signal decomposition is performed for the identified range bin(s) to identify IMF(s). In certain embodiments, VMD is used to decompose a non-stationary signal x(t) into multiple narrow band components $u_k$(t), called IMFs. Equation (10) below describes decomposing the non-stationary signal x(t). Each mode, mode $u_k$(t) is an amplitude and frequency modulated signal as described in Equation (11), below. In Equation (11), $\phi_k$(t) is the phase of the IMF and $A_k$(t) is its envelope.

$$x(t) = \tau_{k=1}^{K} u_k(t) \qquad (10)$$

$$u_k(t) = A_k(t)\cos(\phi_k(t)) \qquad (11)$$

VMD can be described as an optimization algorithm for decomposing an input signal into subcomponents, each of which centers around one specific frequency. The performance of the VMD operation depends on the number of desired subcomponents that are to be decomposed.

It is noted that each identified range bin has 2 time-series, that of the real and imaginary parts of the range bin's CIR. The diagram 430a of FIG. 4C describes the real and imaginary parts of the range bin's CIR of the input signal 432 and multiple IMFs 434 that are decomposed from real and imaginary parts, respectively.

In certain embodiments, each time-series undergoes noise reduction (via a low-pass filter) to reduce noise out of interested frequency band (for normal breathing and heart rate, the range can be from 10-120 Hz, corresponding to a frequency band from 0.1 Hz to 2 Hz). Thereafter the remaining signal is then decomposed using VMD process as illustrated in FIG. 4C. The signal after clutter removal step contains breathing rate signal, heart rate signal, their harmonics and the intermodulation between breathing rate and heart rate. The use of the low-pass filter is to reduce the number of harmonic components, so that the VMD algorithm, which is an optimization process, with a fixed number of IMFs, would be more likely to produce an IMF containing the true Heart Rate signal. The resulting IMFs of all time-series corresponding to the range bins being considered are grouped together to determine the respiratory and heartbeat signals.

Each of the resulting IMF $u_k$(t) centers around one dominant frequency. Using FIG. 4C as an example, from IMF1 to IMF5 (denoted as IMFs 434) the dominant frequency is in the descending order: is IMF5 is the envelop of the signal (lowest frequency), IMF4 which includes the breathing rate signal, IMF3 which includes the $2^{nd}$ harmonic of the breathing rate, IMF2 which includes has the heart rate signal, and IMF1 which includes the residual noise.

In step 440, the electronic device 200 classifies the IMFs into different groups based on the center frequency of each IMF. The electronic device then selects a certain group (that includes one or more of the IMFs) as representing the heart rate and respiration rate of the subject.

For example, each IMF received from the signal decomposition is centered around one dominant frequency ($f_c$), and after converting the IMF to frequency domain, the dominant frequency can be identified as the highest peak in the spectrum. The IMFs for each time series are sorted from high to low dominant frequencies. By processing the IMFs from low to high $f_c$, the electronic device 200 classifies each IMF into different categories based on its $f_c$ as described by the method 440a of FIG. 4D.

In step 442a of FIG. 4D, the electronic device 200 performs signal decomposition of the time series of CIR values to generate one or more IMFs. The time series of CIR values can be the selected range bins corresponding to the location of the subject. The electronic device 200 can generate any number of IMFs. The expression, k is the number of generated IMFs. For this example, it is assumed that the expression, k is five. For example, as illustrated in FIG. 4C, there is one input time series CIR 432 which is used to generate five different IMFs 434.

In step 444, the electronic device 200 sorts the IMFs by their center frequency, such that $f_1 < f_2 < \ldots < f_k$. Once all of the IMFs are sorted, the electronic device 200 in step 444 compares the current IMF index, i, to the value of K (representing the total number of IMFs). When the current IMF index, i, is equal to or is greater than the value K, the electronic device 200 determines the heart rate and respiratory rate of the user based on the center frequencies that are included in each of the groups (such as Group A, Group B, Group C, and Group D)

When the current IMF index, i, is less than k, the electronic device 200 in step 448 determines whether a respiration base frequency was previously identified. When the respiration base frequency was not previously identified (as determined in step 448), the electronic device 200 in step 451 determines whether the current frequency of the IMF, $F_i$, is greater than the minimum respiration frequency. The minimum respiration frequency can be based on a pre-defined threshold.

When the current frequency of the IMF, $F_i$, is greater than the minimum respiration frequency (as determined in step 451) the electronic device sets the current frequency of the IMF, $F_1$, to $f_{resp}$ and adds that IMF to Group A. (step 452) When the current frequency of the IMF, $F_i$, is not greater than the minimum respiration frequency (as determined in step 451) or after the $F_i$ is added to Group A, the current IMF index, i, is increased so the next IMF is inspected and categorized returning to step 444.

It is noted that Group A represents the is respiration IMF since it corresponds to an IMF with lowest $f_c$ that is higher than a threshold $f_{resp\_min}$. Its dominant frequency is $f_{resp}$. This is because of the assumption that the remaining signal at this step only includes respiration signal, heart rate signal, their harmonics and intermodulation's. The typical frequency range of the respiration signal can be 0.1 to 0.8 Hz, the typical frequency range of the heart rate signal can be 0.8 to 2 Hz. Therefore, the IMF with the lowest $f_c$ that is higher than $f_{resp\_min}$ threshold would likely be the respiration IMF. Once this IMF is found, the examination of the next IMFs (with higher center frequency) can proceed based on this newly found base resp. frequency $f_c$.

When the base respiration is found (as determined in step 448), the electronic device 200, in step 454, determines whether the current frequency $f_i$ with the harmonic of the base frequency is close to k times the respiration frequency. The expression k corresponds to the harmonic order: 2 for second-order harmonic and 3 for third-order harmonic. When the difference between $f_i$ and k times the respiration frequency is less than a threshold (as determined in step 454), then $f_i$ is placed in Group B (step 456).

It is noted that Group B represents the respiration harmonics IMF since it includes IMFs with a center frequency, $f_c$, that are near two or three times $f_{resp}$.

Alternatively, if the difference between $f_i$ and k times the respiration frequency is not less than a threshold (as determined in step 454), then in step 458, the electronic device 200 checks if $f_i$ is in the range of the minimum heart rate and a maximum heart rate. In certain embodiments, the minimum heart rate is 48 bpm, and the maximum heart rate is 200 bpm. It is noted that other values for the minimum and maximum heart rate can be used. If $f_i$ is in the range of the minimum heart rate and a maximum heart rate (as determined in step 458), then $f_i$ is placed in Group C (step 460).

It is noted that Group C represents the heart rate IMF since it includes IMFs with a center frequency, $f_c$, in range of $[f_{hr\_min}, f_{hr\_max}] \cdot f_{hr\_min}$, $f_{hr\_max}$ are pre-configured values and a possible values are $f_{hr\_min}$=0.8 Hz, $f_{hr\_max}$=2 Hz Alternatively, if the difference between $f_i$ is not in the range of the minimum heart rate and a maximum heart rate (as determined in step 458), then in step 564, the electronic device 200 determines whether $F_i$ is in the range of the times the minimum heart rate and a maximum heart rate. For example, here, the electronic device 200 determines whether $F_i$ is in the range of 96 to 400. If $f_i$ is in the range of two times the minimum heart rate and two times the maximum heart rate (as determined in step 462), then $f_i$ is placed in Group D (step 462).

It is noted that Group D represents the heart rate harmonics IMF since it includes IMFs with a center frequency $f_c$, in $[2*f_{hr\_min}, 2*f_{hr\_max}]$.

Alternatively, if $f_i$ is not in the range of two times the minimum heart rate and two times the maximum heart rate (as determined in step 462) then the current IMF index, i, is increased so the next IMF is inspected and categorized returning to step 444. Additionally, after $f_i$ is added to Group B (step 456), Group C (step 460), or Group D (step 464), the current IMF index, i, is increased so the next IMF is inspected and categorized returning to step 444.

This grouping process will be repeated for each time series. Therefore, each group will gather IMFs from different time series (which comes from real and imaginary parts of relevant range bins' CIR data).

After the classification, the final output respiration rate and heart rate is determined in step 450. The respiration rate is described in Equation (12) and the heart rate is described in Equation (13), below $$F_{resp} = \text{median}\{f_i | f_i \in GA\} \quad (12)$$

$$F_{hr} = \begin{cases} 0, & GC = GD = \{\} \\ \text{median}\left\{\{f_i | f_i \in GC\} \cup \left\{\frac{f_j}{2} | f_j \in GD\right\}\right\}, & \text{otherwise} \end{cases} \quad (13)$$

Equation (12) describes that the respiration rate is based on a median value of the IMFs of Group A. If there is no peak in Group C and Group D, then the heart rate is zero. Alternatively, if there are peaks in Group C and Group D, then the heart rate is median of the center frequencies of Group D, which is then divided be two and the median of the center frequencies of Group C.

In certain embodiments, an additional filter can be used to smooth the identified heart rate and respiration rate. For example, the smoothing filter can be an exponential weighted moving average. The smoothing filter works on recent frequency estimations from continuous overlapping windows. In one typical implementation, each window has size 20-30 seconds, and moving every 1 second. Suppose $r_i$ is a rate frequency ($F_{resp}$ or $F_{hr}$) estimated from window i is described in Equation (14), below. To avoid excessive convergence time for estimation in the initial windows, a bias correction step can be added to the initial windows (e.g., first 40 windows), as described in Equation (15), below.

$$r_{i,avg} = \beta r_{i-1,avg} + (1-\beta)r_i \quad (14)$$

$$r_{i,avg,bc} = \frac{r_{i,avg}}{1-\beta^i} \quad (15)$$

In certain embodiments, the same or similar classification process is used, but the IMF with the highest peak magnitude in a group of IMFs decomposed from a time series is chosen to be in Group A (corresponding to the respiration IMFs), with the assumption that in scenarios with little movement, the breathing signal is the most dominant signals in the spectrum.

Although FIGS. 4A and 4D illustrate examples for monitoring vitals and the FIGS. 4B and 4C illustrate example diagrams various changes may be made to FIGS. 4A-4D.

For example, while shown as a series of steps, various steps in FIGS. 4A and 4D could overlap, occur in parallel, or occur any number of times.

Figure 5A:
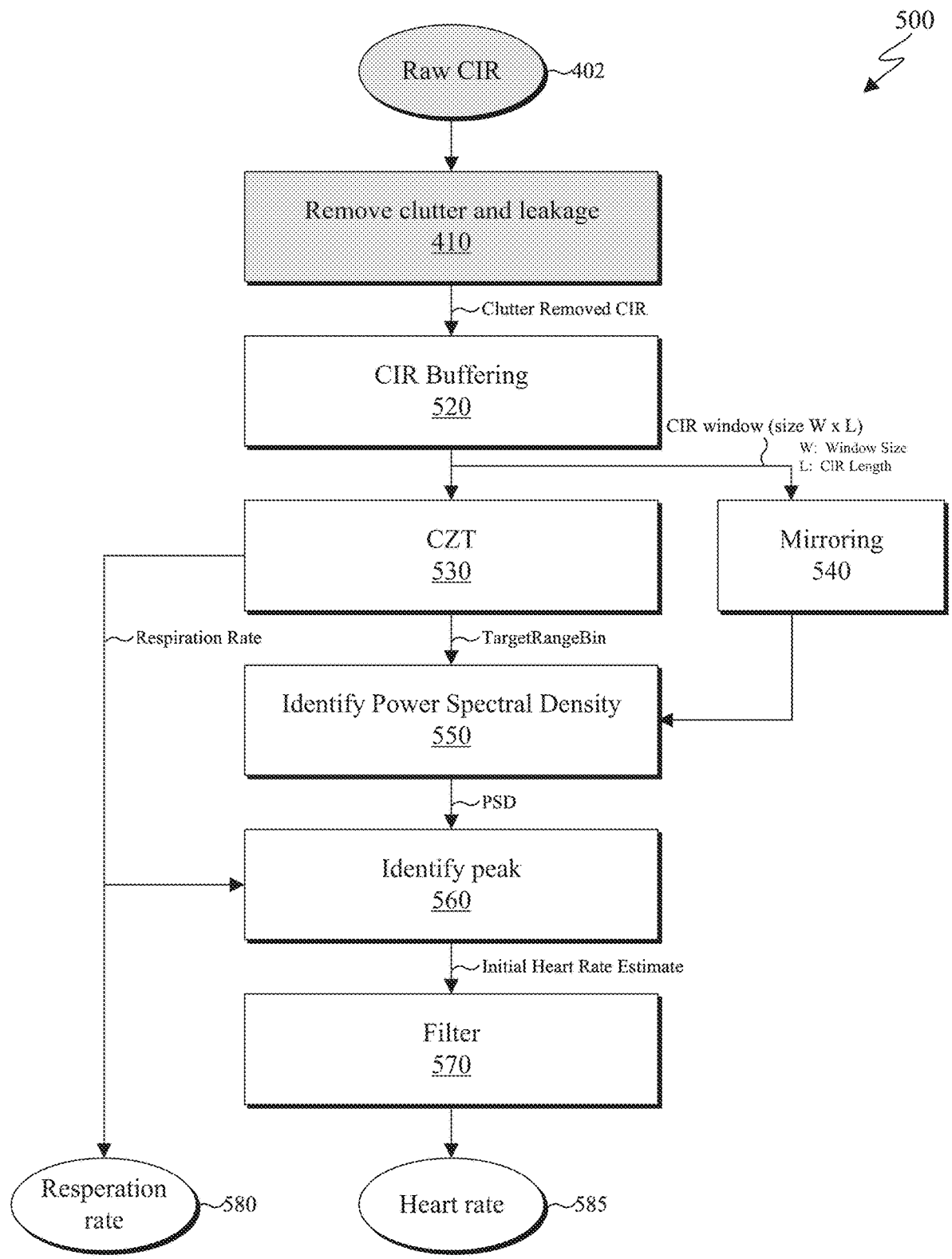
FIG. 5A illustrates an example method for vital monitoring according to embodiments of this disclosure.
Figure 5B:
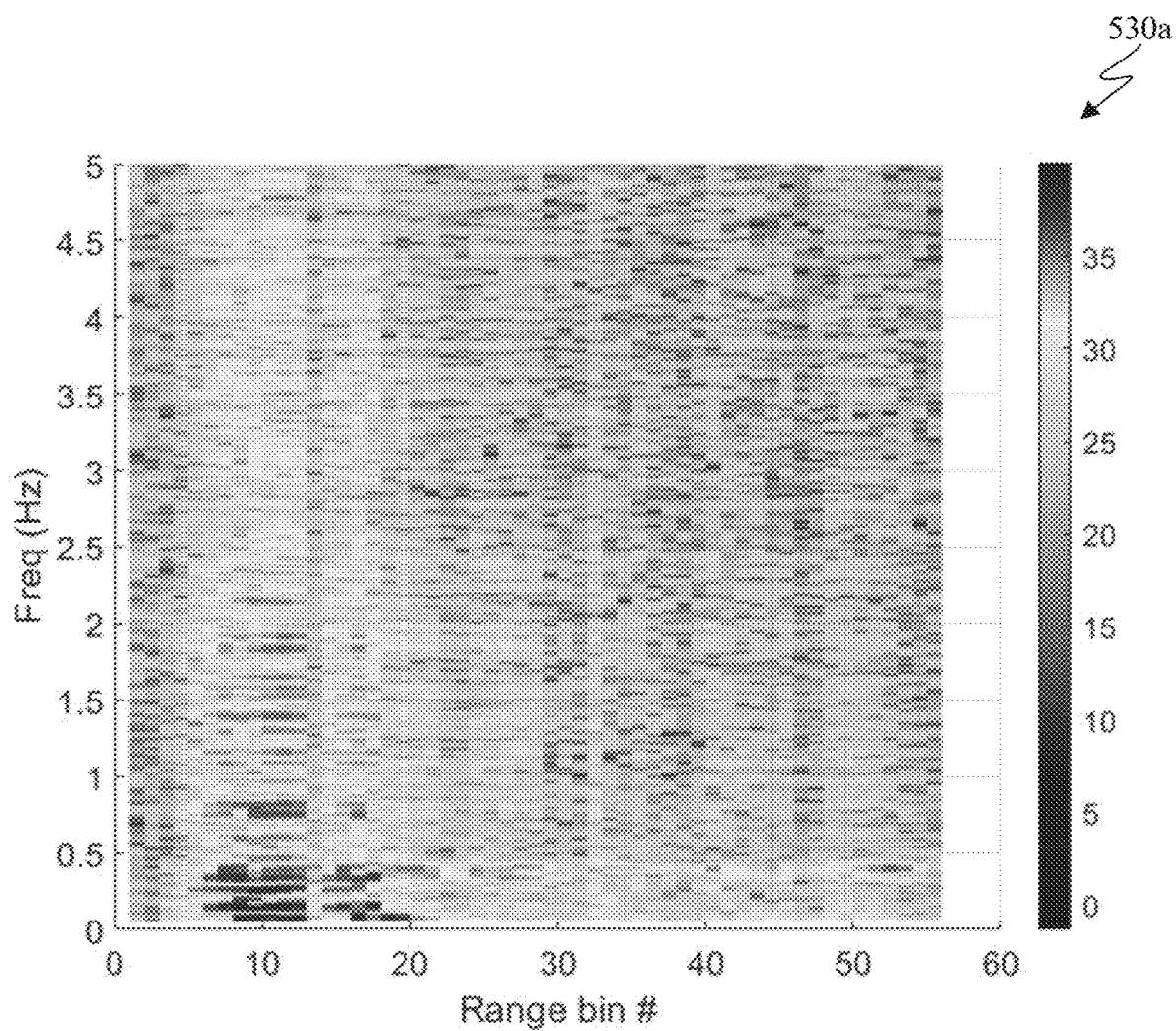
FIG. 5B illustrates an example graph of a frequency spectrum according to embodiments of this disclosure.
Figure 5C:
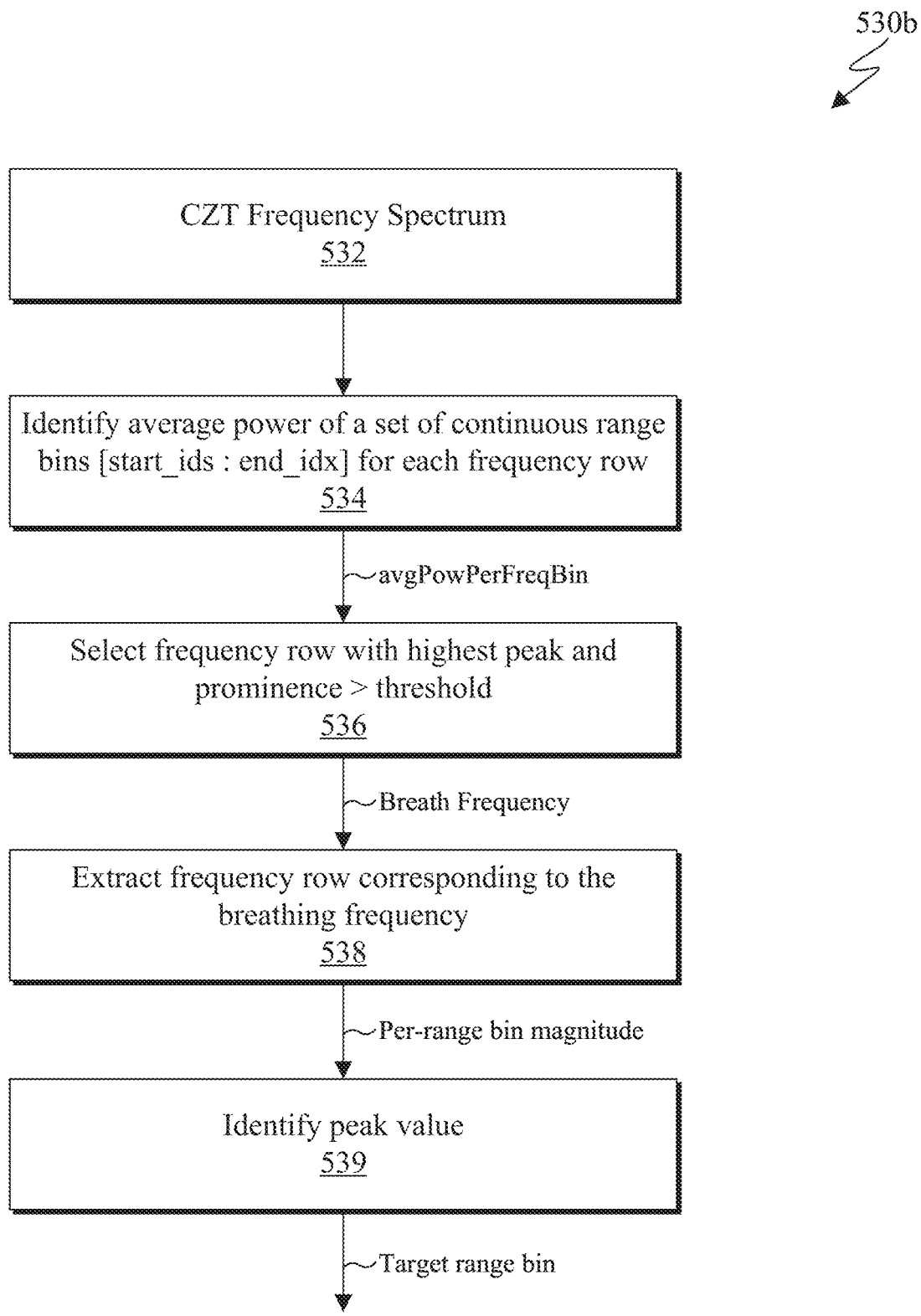
FIG. 5C illustrates an example method for identifying a target range bin and breathing rate according to embodiments of this disclosure.
Figure 5D:
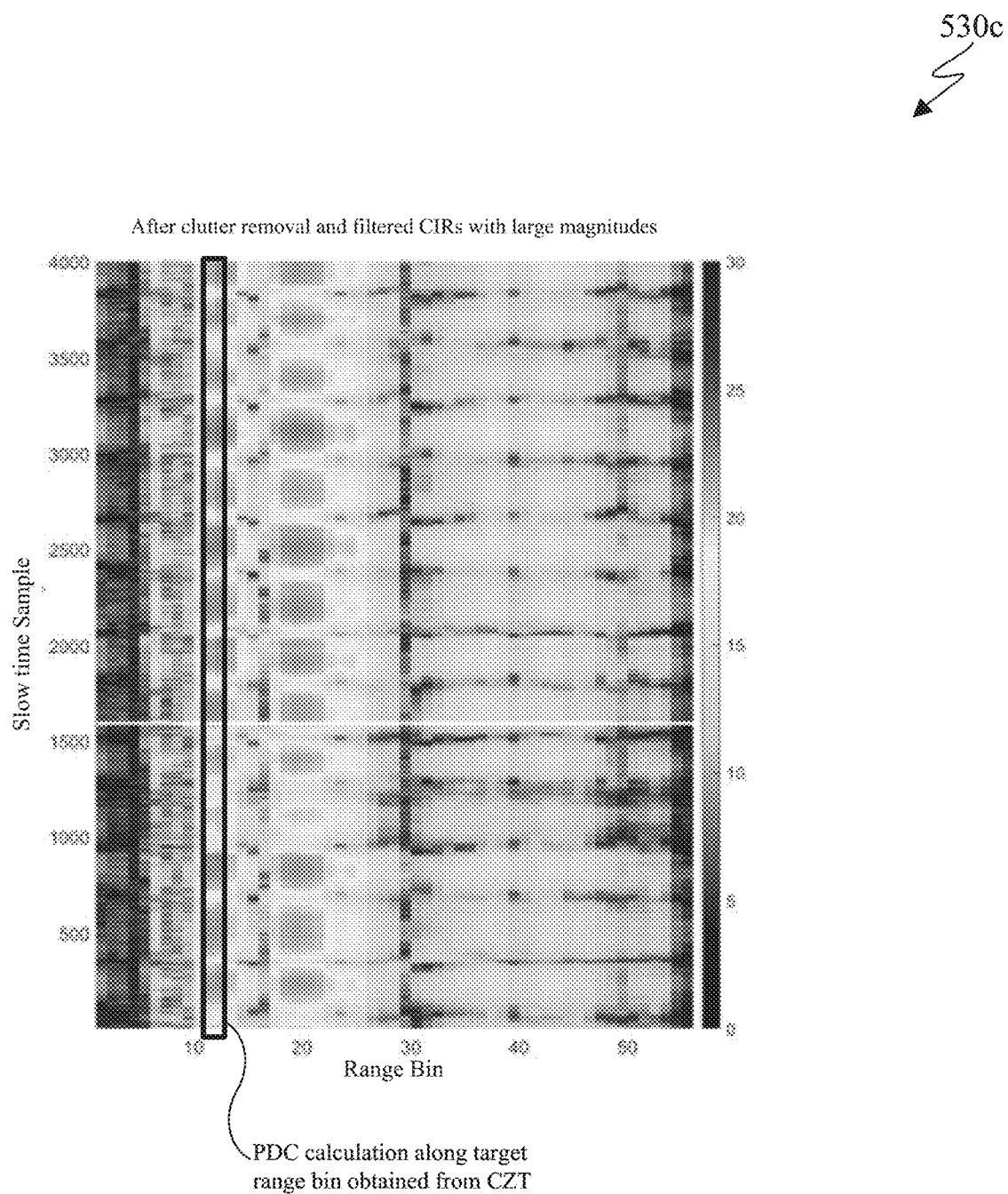
FIG. 5D illustrates an example diagram of graph including a target range bin according to embodiments of this disclosure.
Figure 5E:
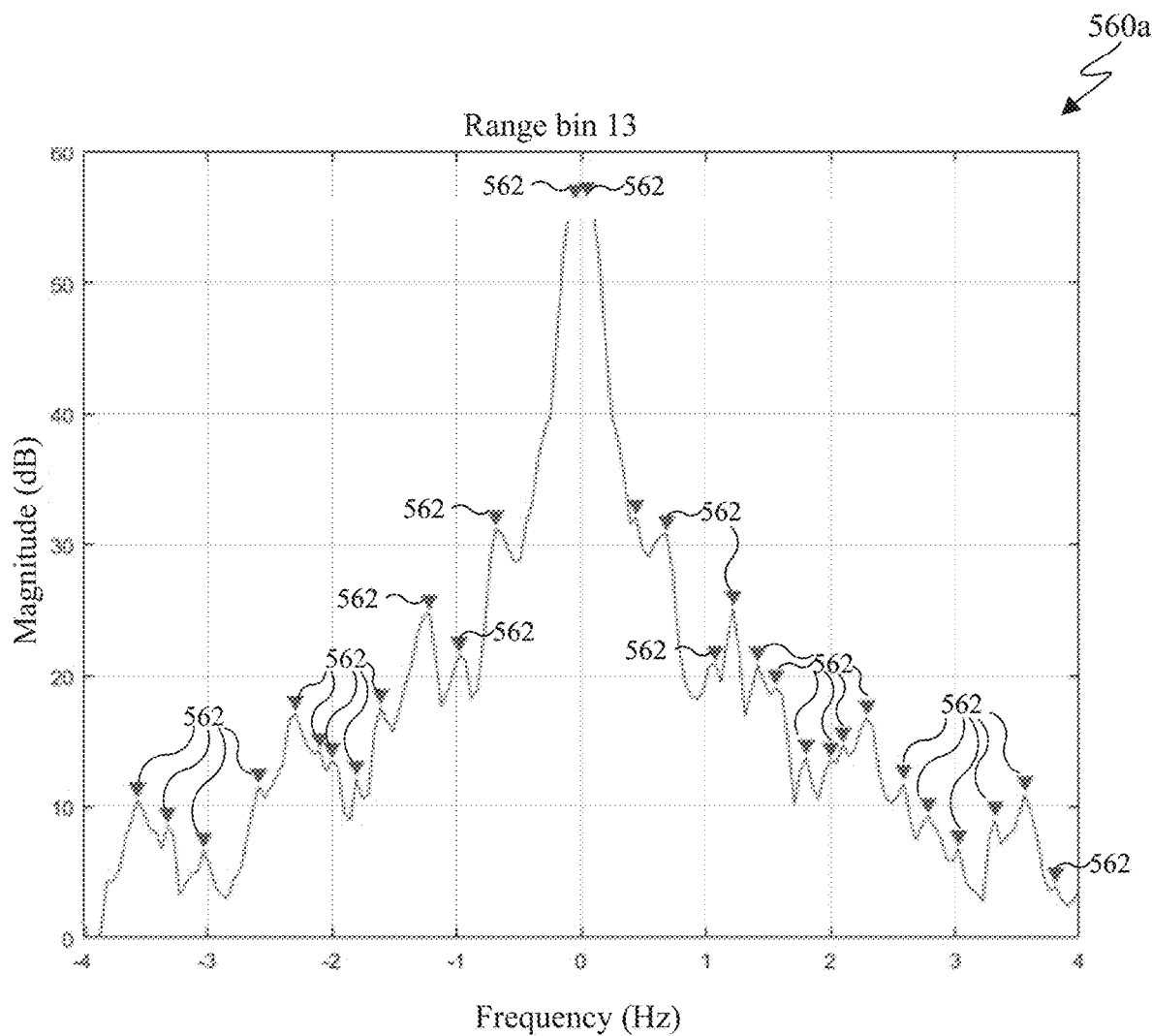
FIG. 5E illustrates an example graph of power spectral density of the target range bin according to embodiments of this disclosure.
Figure 5F:
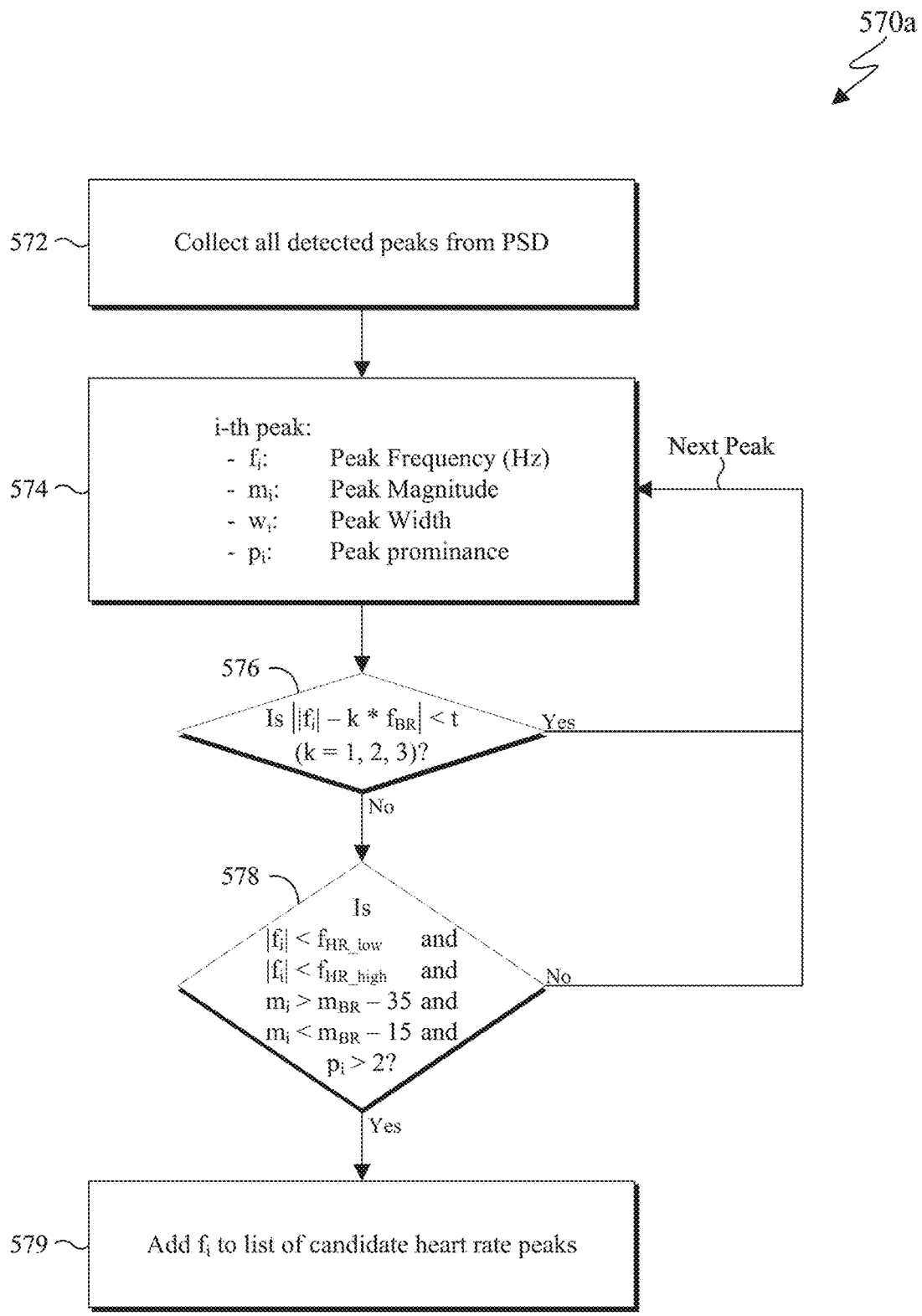
FIGS. 5F and 5G illustrate example methods for identifying heart rate from the power spectral density of the target range bin according to embodiments of this disclosure.
Figure 5G:
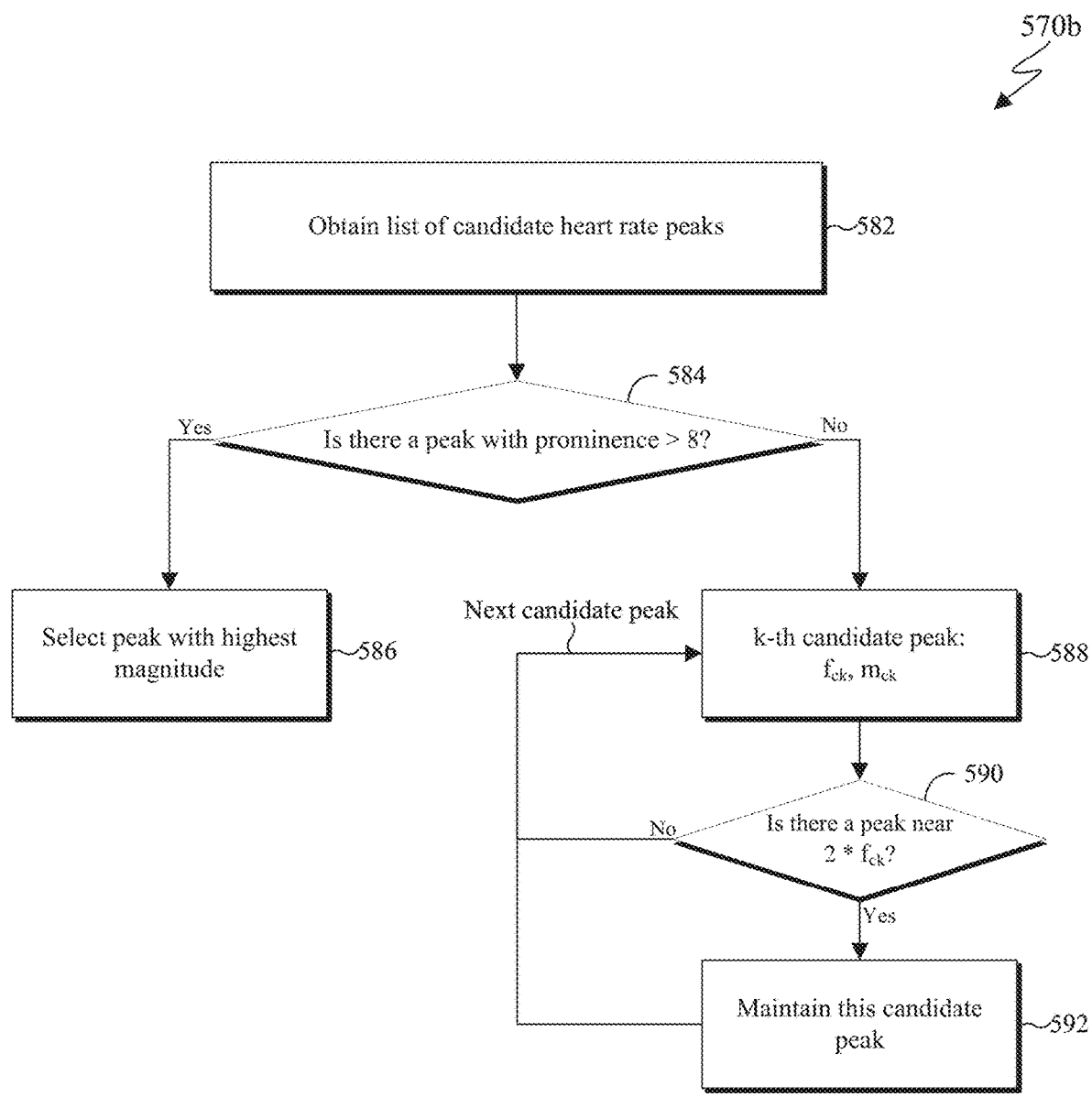
Figure 5H:
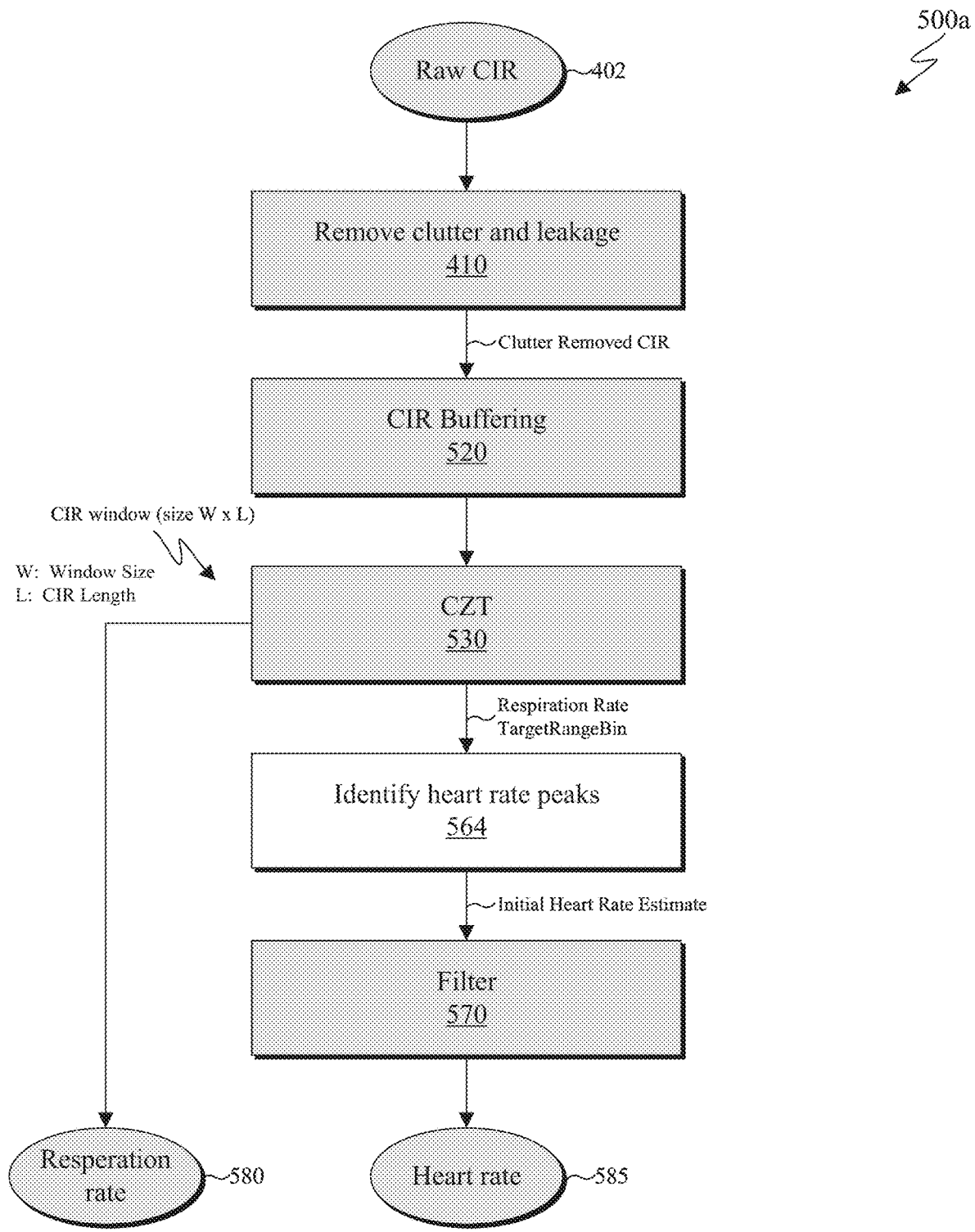
FIG. 5H illustrates an example method for vital monitoring according to embodiments of this disclosure.

FIG. 5A illustrates an example method 500 for vital monitoring according to embodiments of this disclosure. FIG. 5B illustrates an example graph 530a of a frequency spectrum according to embodiments of this disclosure. FIG. 5C illustrates an example method 530b for identifying a target range bin and breathing rate according to embodiments of this disclosure. FIG. 5D illustrates an example diagram of graph 530c including a target range bin according to embodiments of this disclosure. FIG. 5E illustrates an example graph 560a of power spectral density of the target range bin according to embodiments of this disclosure. FIGS. 5F and 5G illustrate example methods 570a and 570b, respectively, for identifying heart rate from the power spectral density of the target range bin according to embodiments of this disclosure. FIG. 5H illustrates an example method 500a for vital monitoring according to embodiments of this disclosure. The embodiments of FIGS. 5A-5H are for illustration only and other embodiments can be used without departing from the scope of the present disclosure.

The method 500 as illustrated in FIG. 5A, the method 530b as illustrated in FIG. 5C, the method 570a as illustrated in FIG. 5F, the methods 570b as illustrated in FIG. 5G and the method 500a as illustrated in FIG. 5H are described as implemented by any one of the client device 106-114 of FIG. 1, the server 104 of FIG. 1, the electronic device 300 of FIG. 3, and can include internal components similar to that of electronic device 200 of FIG. 2. However, the method 500 as shown in FIG. 5A, the method 530b as shown in FIG. 5C, the method 570a as shown in FIG. 5F, the methods 570b as shown in FIG. 5G, and the method 500a as shown in FIG. 5H could be used with any other suitable electronic device and in any suitable system, such as when performed by the electronic device 200. For ease of explanation, the methods of FIGS. 5A, 5C, 5F, 5G, and 5H are described as being performed by the electronic device 200 of FIG. 2.

The method 500, as illustrated in FIG. 5A, and the method 500a, as illustrated in FIG. 5H, describe detecting and monitoring vitals of a subject. It is noted that certain steps in FIG. 5A corresponds to the various steps with similar reference numbers of FIG. 4A. Similarly, certain steps in FIG. 5H corresponds to the various steps with similar reference numbers of FIGS. 4A and 5A.

As described above, in step 410, the electronic device 200 removes clutter and leakage from received raw CIR 402. The raw CIR 402 can be IR-UW radar signals which are reflections of a transmitted pulses.

In step 520, clutter removed CIR is buffered. For example, the electronic device 200 segments the CIR into multiple CIR windows of a predefined size. The breathing and heart rate analysis is performed on a window-by-window basis. Each window is a two-dimensional (2D) matrix of size W×L, where W is the number of slow time samples (or window size), and L is the length of the CIR for each time sample.

In step 530, the electronic device 200 applies a CZT to each of the clutter removed CIR windows. The electronic device 200, using the CZT, identifies the target range bin corresponding to the distance to the subject as well as the respiration rate of the subject.

CZT provides a high-resolution spectrum for achieving high accuracy breathing rate estimation. For example, the resolution of CZT can be set more flexibly by setting a frequency band of interest $[f_{min}, f_{max}]$ and the number of CIR samples. The frequency resolution of CZT is described in Equation (16), below. For example, if $f_{min}$ is set to 0.05 Hz, $f_{max}$ is set to 5 Hz, and there are 4000 samples, then the frequency resolution of would be 0.0012 Hz or 0.072 bpm.

$$\text{Frequency Resolution} = \frac{f_{max} - f_{min}}{\#samples} \tag{16}$$

In contrast Fast Fourier transform (FFT) provides a lower resolution since it is constrained by Equation (17). For example, with sampling rate=50 Hz, FFT length=512 (for a CIR window of length 20 seconds), the FFT bin width (resolution)=0.0977 Hz=5.86 bpm.

$$FFT \text{ bin width} = \frac{\text{sample rate}}{FFT \text{ length}} \tag{17}$$

In certain embodiments, CZT is used instead of a FFT due to its resolution.

The graph 530a as illustrated in FIG. 5B illustrates an example, CZT frequency spectrum. The frequency spectrum has frequency as the vertical axis and the range bin ID as the horizontal axis. Here the range bin defines the distance from the radar, where each range bin represents an even distance interval based on the UWB antenna's range resolution. For example, one range bin can represent 15 cm. Each cell shows the energy corresponding to a specific range bin and a specific frequency.

The electronic device 200 uses the CZT frequency spectrum, to identify a target range bin and breathing rate. The method 530b as illustrated in FIG. 5C describes process for identifying the target range bin and breathing rate of the subject.

In step 532 of FIG. 5C the electronic device 200 generates the CZT frequency spectrum, such as the graph 530a as illustrated in FIG. 5B.

In step 534, for each frequency row, the electronic device 200 identifies the average power of a set of continuous range bins, from start_idx to end_idx. The average power values are stored in a variable named "avgPowPerFreqBin", which is an array of size nFreqBins (number of frequency bins).

In step 536, the electronic device 200 identifies the highest peak from "avgPowPerFreqBin." If this peak has a prominence value greater than a predefined threshold, the corresponding frequency row will be output as the breathing frequency. Otherwise, when this peak's prominence is weak, it indicates there is no dominant breathing frequency component and the current CZT frequency spectrum includes mostly noise, so this step returns no breath frequency and the method 530b (and step 530 of the method 500 of FIG. 5A) terminates here.

After the breath frequency is identified (as identified in step 536), the electronic device 200 in step 538 extracts the frequency row corresponding to the breathing frequency, resulting in a one-dimensional (1D) array of per-range bin magnitudes.

In step 539, the electronic device 200 identifies the highest peak. Here the peak (highest) magnitude value is identified, and the corresponding range bin is output as the target range bin.

As such, the electronic device 200 identifies the target range bin and breathing rate. It is noted that the breathing rate is one of the final outputs, and as described below the breathing rate is used for finding the heart rate. The target range bin, as described below, is used to identify the Power spectral density.

After the breathing rate is identified, the electronic device 200 then identifies to heart rate. To identify the heart rate, the electronic device 200, in step 550 identifies a PSD for mirrored CIR window (step 540) at target range bin. In certain embodiments, the Welch's power spectral density estimate can be used.

For example, in step 540, the electronic device 200 mirrors the CIR window (generated from step 520) by generating a replica of the current CIR window that is flip and concatenated to the end of the current CIR, along the slow time dimension. Mirroring effectively doubles the number of samples, for improving the frequency resolution of the PSD. Depending on the range bin resolution, the range bin to calculate PSD is determined accordingly from the target range bin identified in step 530. For example, when range bin resolution is 15 cm, the heart rate signal is likely within the same range bin as target range bin, thus the PSD is calculated for the target range bin (as shown in the figure below). When the range bin resolution is much smaller, PSD for several range bins around the target range bin can be used.

In certain embodiments, a two-sided PSD is used to increase visibility of the Heart rate peaks, as illustrated in the graph 560a of FIG. 5E.

In step 560, the electronic device 200 identifies certain peaks (such as peaks 562) of the PSD for identifying the heart rate. For example, the graph 560a of FIG. 5E is a two-sided PSD that is used for determining Heart Rate. The electronic device 200 identifies candidate peaks (such as peak 562) from, including breathing rate peaks, breathing harmonic peaks, heart rate peaks and heart rate harmonic peaks, together with peaks formed by the intermodulation between heart rate and breath rate. It is noted that the heart rate peak can be 20-30 dB lower than the breathing rate peak. Additionally, the peak corresponding to the heart rate can be masked by harmonics of the breathing rate. For example, a breathing rate harmonic could be between 0.1-1 Hz while the heart rate can be 0.8-2 Hz.

In step 570, using a series of filters, described in FIGS. 5F and 5G, the electronic device 200 identifies one or more peaks from the two-sided PSD, which correspond to the heart rate of the subject. That is, the electronic device 200 filters out (ignores) any peaks that do not correspond to the heart rate of the user. The electronic device then outputs the respiration rate 580 and the heart rate 585 of the subject. Additionally, before outputting the heart rate 585, the electronic device 200 can further filter the heart rates by applying a smoothing filter to reduce fluctuation of the detected heart rate The method 570a of FIG. 5F describes that the identified peaks 562 are filtered (step 570 of FIG. 5A) based on their own properties, and thereafter the method 570b of FIG. 5G describes that any remaining peaks are further filtered by the existence of second harmonics.

Referring to FIG. 5F, the electronic device 200 identifies and collects all of the detected peaks (such as peaks 562 of FIG. 5E) from the PSD (step 572). In step 574, the electronic device identifies various properties associated with a peak at each iteration. For example, for peak, i, the electronic device determines the peak frequency (Hz), peak magnitude (dB), peak width (Hz), and peak prominence. The prominence of a peak measures how much the peak stands out due to its intrinsic height and its location relative to other peaks. The properties of the peaks can be stored in a memory, such as the memory 260 of FIG. 2.

In step 576, the electronic device 200 checks each peak to see if it is a breathing rate peak or a breathing harmonic peak. For example, the electronic device 200 determines whether the absolute frequency of a peak is near k times the detected breathing rate (as determined in step 530 of FIG. 5A). That is, the electronic device compares the difference between the frequency of associated with particular peak to k times a breathing frequency to a threshold. The value of k can be a predefined value. For a non-limiting example, the value of K can be 1, 2, or 3. Peaks that satisfy this condition are removed as they do not correspond to the heart rate, and the next peak is inspected In step 578, the peak is checked to see whether it satisfies the following three conditions. First, the electronic device 200 determines whether the peak frequency between the typical range of heart rate $[f_{HRlow}, f_{HRhigh}]$. The frequency of HRlow and HRhigh can be predefined. If the peak frequency is outside the range, the next peak is selected. The electronic device 200 also determines whether the peak magnitude is within a certain range determined with respect to the with respect to the breathing rate magnitude. For example, if the peak magnitude $m_i$ satisfies the condition $m_i > m_{BR}-35$ (dB) and $m_i < m_{BR}-15$ (dB), then the peak is not filtered out. if the properties of the peak do not satisfy the two conditions ($m_i > m_{BR}-35$ (dB) and $m_i < m_{BR}-15$ (dB)), then that peak is filtered out and the electronic device 200 selects the next peak. The electronic device 200 also determines whether the peak prominence greater than a predefined threshold. In certain embodiments, the threshold can be two. This condition ensures noise peaks are rejected.

In step 579, each peak of the PSD that satisfies the conditions of steps 576 and 578 are added to a list of candidate heart rate peaks. This process repeats until all of the peaks of the PSD are inspected and either filtered out or included in the list of candidate heart rate peaks.

Referring to FIG. 5G, the electronic device 200 in step 582 obtains the list of candidate heart rate peaks as identified in step 579 of FIG. 5F. In step 584, the electronic device 200 determines whether there is a peak from the list of candidate heart rate peaks with prominence greater than a predefined threshold. In certain embodiments, the predefined threshold is the value of eight. When a peak has a prominence greater than a predefined threshold indicates that the heart rate signal is not masked by the breathing harmonics and easily visible in the spectrum. If such one or more peaks from the list of candidate heart rate peaks have a prominence greater than the predefined threshold (as determined in step 584), then in step 586, the peak with the highest magnitude is selected as the output heart rate $f_{hr}$.

Alternatively, if no peaks from the list of candidate heart rate peaks have a prominence greater than the predefined threshold (as determined in step 584), the in step 588, the electronic device 200 inspects the peaks t their second harmonics. Suppose the k-th candidate peak has frequency $f_{ck}$, in step 590, the electronic device 200 determines whether there is a peak near two times the frequency $f_{ck}$. If the electronic device 200 determines that is a peak near two times the frequency $f_{ck}$, this peak is maintained (step 592). The reason is the true heart rate peak is likely caused another $2^{nd}$ harmonic peak on the spectrum.

After the peak is maintained (step 592) or the electronic device 200 determines that there is no peak near two times the frequency $f_{ck}$ (as determined in step 590), another candidate peak is selected and steps 588, 590, and 592 are repeated until all candidate heart rate peaks from the list are inspected. It is noted that if there is no candidate left in the list and no candidates maintained in step 592 the electronic device 200 generates an output that there is detectable heart rate.

In certain embodiments, if there are more than two candidate peaks left (maintained in step 590), the electronic device 200 selects the two candidate peaks that have the largest harmonic peak magnitudes. Then the electronic device 200 examining the spectrum at their corresponding $3^{rd}$ harmonic frequency of the two candidate peaks. The final output heart rate peak would be the peak that has: (i) a peak exists near its corresponding $3^{rd}$ harmonic frequency (with frequency $f_{3rdharmonic}$ and magnitude $m_{3rdharmonic}$), and (ii) $m_{3rdharmonic}$ is the highest among candidates.

In the above steps, at each time step there would be a possible output of a heart rate or an indication that no heart rate was detected (such as when the heart rate is close to a breathing rate harmonic frequency). Embodiments of the present disclosure take into consideration that the output heart rate, when available, could also be inaccurate due to noise or mischaracterization of peaks. Accordingly, before outputting the heart rate 585 (FIG. 5A), the electronic device 200 can further filter the heart rates by applying a filter to reduce fluctuation of the detected heart rate (step 570). The electronic device 200 can use one or more types of filter such as an average filter (taking mean of the last N estimations), a median filter (taking median of the last N estimations), an outlier rejection filter (removing the estimations in the last N estimations that are too far from the mean/median of the last N estimations, then taking mean/median of the remaining estimations), or the like.

Although FIGS. 5A, 5C, 5F, 5G, and 5H, illustrate examples for monitoring vitals and the FIGS. 5B, 5D, 5E illustrate example diagrams various changes may be made to FIGS. 5A-5H. For example, while shown as a series of steps, various steps in FIGS. 5A, 5C, 5F, 5G, and 5H could overlap, occur in parallel, or occur any number of times.

Figure 6:
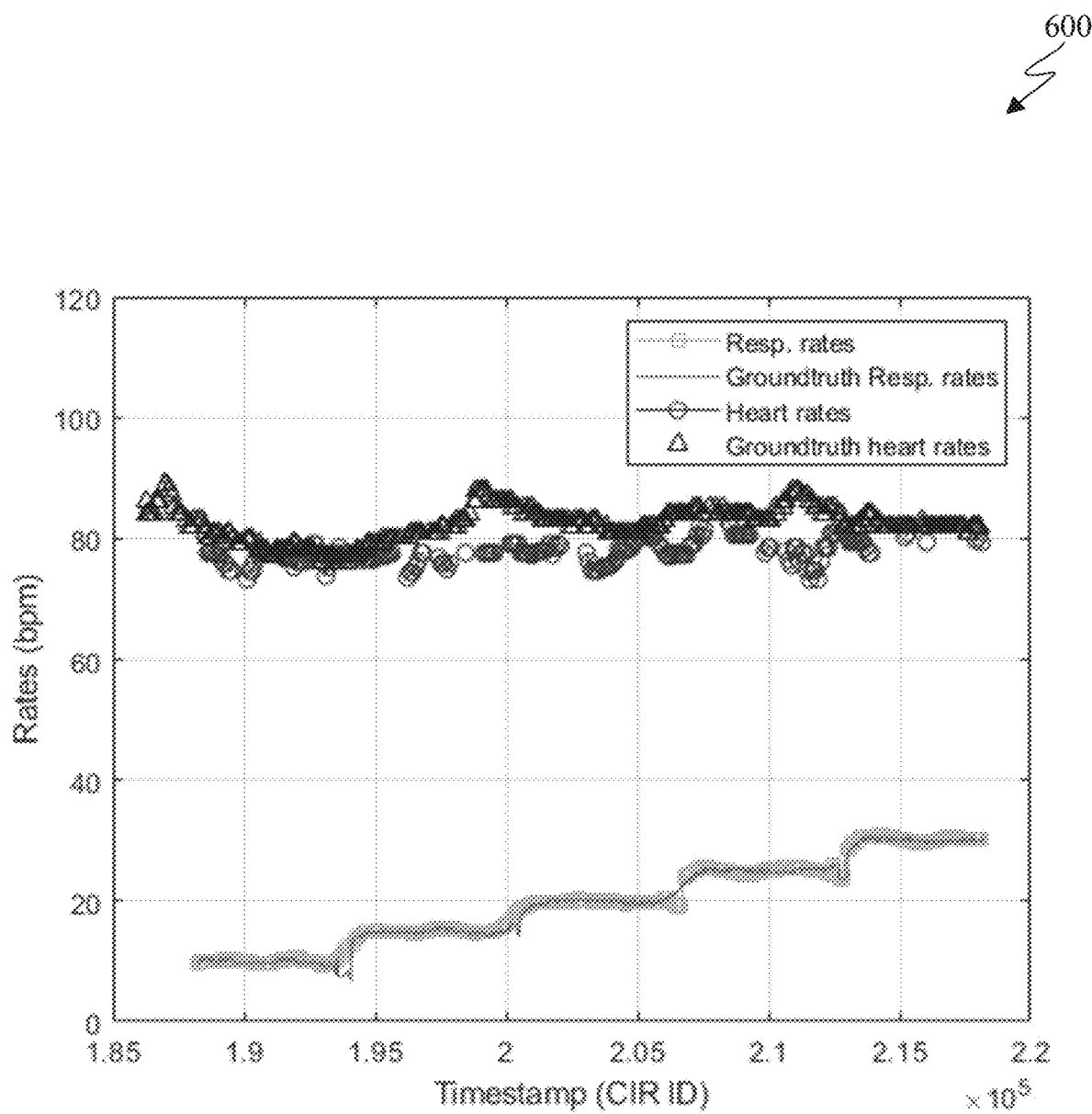
FIG. 6 illustrates an example diagram depicting vital monitoring results according to embodiments of this disclosure.

FIG. 6 illustrates an example diagram 600 depicting vital monitoring results according to embodiments of this disclosure. The embodiments of FIG. 6 is for illustration only and other embodiments can be used without departing from the scope of the present disclosure.

The diagram 600 of FIG. 6 can be represents results generated using the method 400 as illustrated in FIG. 4A, the method 500 as illustrated in FIG. 5A, or the method 500a as illustrated in FIG. 5H. The diagram 600 can be generated by any one of the client device 106-114 of FIG. 1, the server 104 of FIG. 1, the electronic device 300 of FIG. 3, and can include internal components similar to that of electronic device 200 of FIG. 2. Although diagram 600 depicts example results of monitored vitals, various changes may be made to FIG. 6, such as more or less vitals can be monitored.

The diagram 600 illustrates example results using an electronic device equipped with UWB radar capabilities. Radar signals are directed towards the chest of the individual while breathing normally. The diagram 600 depicts a comparison of the heart rate and breathing rate as determined by the various embodiments to ground truth heart rate using a heart rate monitoring device and ground truth respiration rate using a belt mounted on the chest of the subject, respectably, both of which are in contact with the use.

Figure 7:
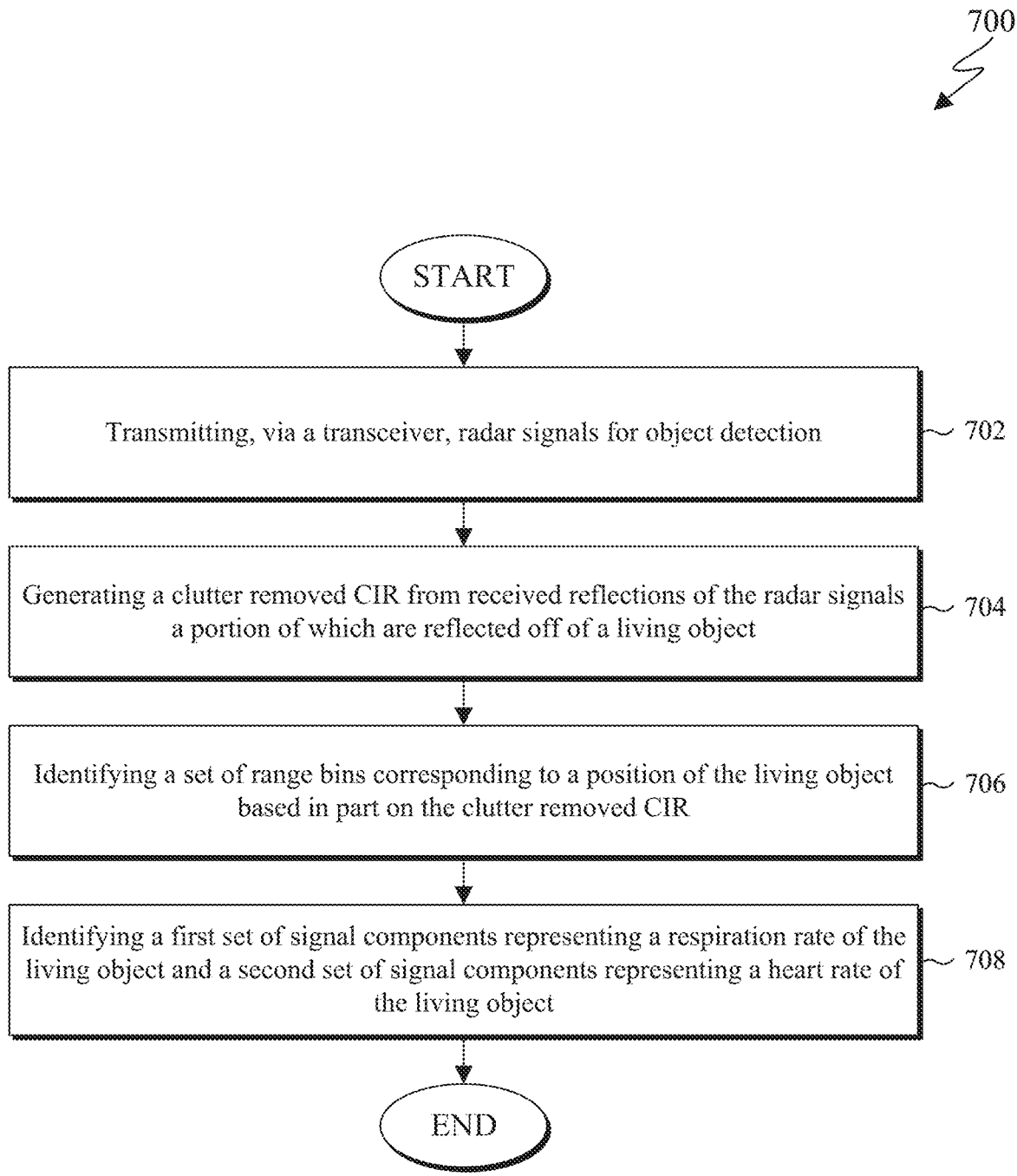
FIG. 7 illustrates an example method for vital monitoring according to embodiments of this disclosure.

FIG. 7 illustrates an example method for vital monitoring according to embodiments of this disclosure. The embodiments of the method 700 of FIG. 7 is for illustration only. Other embodiments can be used without departing from the scope of the present disclosure.

The method 700 is described as implemented by any one of the client device 106-114 of FIG. 1, the electronic device 300 of FIG. 3, and can include internal components similar to that of electronic device 200 of FIG. 2. However, the method 700 as shown in FIG. 7 could be used with any other suitable electronic device and in any suitable system, such as when performed by the electronic device 200.

In step 702, an electronic device (such as the electronic device 200) transmits signals for vital sign detection or monitoring. The electronic device 200 can also receive the transmitted signals that reflected off of an object via a radar transceiver, such as the radar transceiver 270 of FIG. 2. In certain embodiments, the signals are UWB radar signals, such as IR-UWB signals.

In step 704, the electronic device 200 generates a clutter removed CIR from the received reflections of the radar signals. In certain embodiments, a portion of the received reflections are reflected off of a living object. To generate the clutter removed CIR, the electronic device 200 can remove clutter from the radar signals based on a predefined parameter using a high-pass filter.

In step 706, the electronic device 200 identifies a set of range bins corresponding to a position of the living object. The range bins are identified based in part on the clutter removed CIR.

In certain embodiments, to identify the set of range bins corresponding to the position of the living object, the electronic device 200 can identify standard deviation values for range bins of the clutter removed CIR. Thereafter the electronic device 200 compares the standard deviation values corresponding to the range bins to identify one or more of the range bins based on a predefined criteria as the set of range bins corresponding to the position of the living object.

In certain embodiments, to identify the set of range bins corresponding to the position of the living object, the electronic device 200 can identify total energy values for range bins of the clutter removed CIR. Thereafter the electronic device 200 compares the total energy values corresponding to the range bins to identify one or more of the range bins based on a predefined criteria as the set of range bins corresponding to the position of the living object.

In certain embodiments, to identify the set of range bins corresponding to the position of the living object, the electronic device 200 can segment the clutter removed CIR into clutter removed CIR windows of a predefined size. The electronic device 200 generates the frequency spectrum from the clutter removed CIR windows using a chirp-Z transform. The set of range bins are identified based on properties of the frequency spectrum. For example, the electronic device 200 can identify, from the frequency spectrum, an average power of a set of continuous range bins for each frequency row of a plurality of frequency rows. The electronic device 200 can select a first frequency row from the plurality of frequency rows that includes a peak that satisfies a predefined criteria and includes a prominence greater than a threshold. The electronic device can then identify a range bin with a highest magnitude value from the first frequency row and include the identified range bin in the set of range bins corresponding to the position of the living object.

In step 708, the electronic device 200 identifies a first set of signals representing the respiration rate of the living object as well as a second set of signals representing the heart rate of the living object.

In certain embodiments, the electronic device 200 in a first operation, identifies the first and second sets of signals using VMD that decomposes a non-stationary signal of the set of range bins into sub-components representing respiration and heart rates. For example, the electronic device 200 can decompose, using VMD, real and imaginary parts of each range bin of the set of range bins into multiple narrow band components, wherein each of the narrow band components are centered around a respective frequency. The electronic device 200 can also classify the multiple narrow band components into different groups corresponding to different frequency ranges. The different groups can include a breathing rate group, a respiration harmonics group, a heart rate group, and a heart rate harmonics group. The electronic device 200 can then identify the respiration rate and the heart rate based on properties of the different groups. For example, the electronic device 200 can generate an output representing a final respiration rate based on a median value of the breathing rate group. For example, the electronic device 200 can generate an output representing a final heart rate based on a median value of the heart rate group and a median value of a portion of the heart rate harmonics group.

In certain embodiments, the electronic device 200 in a second operation, identifies the first set of signal components from a generated frequency spectrum and identifies the second set of signal components based on properties of a generated power spectrum density using the identified range bins. After clutter removed CIR is segmented (step 706), the electronic device 200 can combine a selected clutter removed CIR window with a mirrored copy of the selected clutter removed CIR window to generate a modified CIR window. The electronic device 200 then generates the power spectrum density from the modified CIR window bins. The electronic device 200 can then identify (i) the first set of signal components based on the properties of the frequency spectrum, and (ii) the second set of signal components based on the first set of signal components and properties of the power spectrum density.

In the second operation, the electronic device 200 can identify the respiration rate based on a frequency value corresponding to the first frequency row that is selected from the frequency power spectrum generated in step 706.

In the second operation, the electronic device 200 can identify the heart rate identify a set of peaks of the power spectrum density, wherein the set of peaks includes breathing rate peaks, breathing harmonic peaks, heart rate peaks, and heart rate harmonic peaks. The electronic device 200 then removes one or more peaks that corresponds to the respiration rate from the set of peaks. After removing the one or more peaks, the electronic device 200 identifies a set of candidate heart rate peaks from the set of peaks that satisfy a set of predefined conditions. The electronic device 200 then identifies the heart rate from the set of candidate heart rate peaks based on properties of the set of candidate heart rate peaks including heart rate harmonics.

Although FIG. 7 illustrates an example method 700, various changes may be made to FIG. 7. For example, while the method 700 is shown as a series of steps, various steps could overlap, occur in parallel, occur in a different order, or occur multiple times. In another example, steps may be omitted or replaced by other steps.

The above flowcharts illustrate example methods that can be implemented in accordance with the principles of the present disclosure and various changes could be made to the methods illustrated in the flowcharts herein. For example, while shown as a series of steps, various steps in each figure could overlap, occur in parallel, occur in a different order, or occur multiple times. In another example, steps may be omitted or replaced by other steps.

Although the figures illustrate different examples of user equipment, various changes may be made to the figures. For example, the user equipment can include any number of each component in any suitable arrangement. In general, the figures do not limit the scope of this disclosure to any particular configuration(s). Moreover, while figures illustrate operational environments in which various user equipment features disclosed in this patent document can be used, these features can be used in any other suitable system. None of the description in this application should be read as implying that any particular element, step, or function is an essential element that must be included in the claims scope.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An electronic device for contactless vital sign monitoring, the electronic device comprising:
a transceiver; and
a processor operably connected to the transceiver, the processor configured to:
transmit, via the transceiver, radar signals for object detection;
generate a clutter removed channel impulse response (CIR) from received reflections of the radar signals, a portion of which are reflected off of a living object;
identify a set of range bins corresponding to a position of the living object based in part on the clutter removed CIR, wherein the portion of the clutter removed CIR includes a set of non-stationary signals that respectively correspond to each range bin among the set of range bins; and
identify a first set of signal components representing a respiration rate of the living object and a second set of signal components representing a heart rate of the living object,
wherein to identify the first set of signal components and the second set of signal components, the processor is further configured to:
in a first operation, identify the first set of signal components and the second set of signal components using variational mode decomposition (VMD) that decomposes each non-stationary signal of the set of non-stationary signals into subcomponents representing the respiration rate and the heart rate, or
in a second operation, identify the first set of signal components from a generated frequency spectrum and identify the second set of signal components based on properties of a generated power spectrum density using the set of range bins; and
wherein to use the VMD that decomposes each non-stationary signal into subcomponents representing the respiration rate and the heart rate, the processor is further configured to:
decompose, using VMD, a real part of each non-stationary signal into multiple narrow band components, wherein each of the narrow band components is centered around a respective frequency; and
decompose, using VMD, an imaginary part of each non-stationary signal into the multiple narrow band components centered around the respective frequencies.

2. The electronic device of claim 1, wherein to generate the clutter removed CIR, the processor is configured to remove clutter from received radar signals based on a predefined parameter using a high-pass filter.

3. The electronic device of claim 1, wherein to identify the set of range bins corresponding to the position of the living object, the processor is configured to:
identify standard deviation values for range bins of the clutter removed CIR; and
compare the standard deviation values corresponding to the range bins to identify one or more of the range bins based on a predefined criteria as the set of range bins corresponding to the position of the living object.

4. The electronic device of claim 1, wherein to identify the set of range bins corresponding to the position of the living object, the processor is configured to:
identify total energy values for range bins of the clutter removed CIR; and
compare the total energy values corresponding to the range bins to identify one or more of the range bins based on a predefined criteria as the set of range bins corresponding to the position of the living object.

5. The electronic device of claim 1, wherein to identify the first set of signal components and the second set of signal components using the first operation, the processor is configured to:
classify the multiple narrow band components of the decomposed real and imaginary parts of each non-stationary signal of the set of non-stationary signals into different groups corresponding to different frequency ranges; and
identify the respiration rate and the heart rate based on properties of the different groups.

6. The electronic device of claim 5, wherein:
the different groups include a breathing rate group, a respiration harmonics group, a heart rate group, and a heart rate harmonics group; and
the processor is further configured to:
generate an output representing a final respiration rate based on a median value of the breathing rate group, and
generate an output representing a final heart rate based on a median value of the heart rate group and a median value of a portion of the heart rate harmonics group.

7. The electronic device of claim 1, wherein to perform the second operation, the processor is further configured to:
segment the clutter removed CIR into clutter removed CIR windows of a predefined size;
generate the frequency spectrum from the clutter removed CIR windows using a chirp-Z transform; and
identify the set of range bins based on properties of the frequency spectrum.

8. The electronic device of claim 7, wherein to identify the set of range bins based on properties of the frequency spectrum and the respiration rate, the processor is configured to:
identify, from the frequency spectrum, an average power of a set of continuous range bins for each frequency row of a plurality of frequency rows;
select a first frequency row from the plurality of frequency rows that includes a peak that satisfies a predefined criteria and includes a prominence greater than a threshold;
identify the respiration rate based on a frequency value corresponding to the first frequency row;
identify a range bin with a highest magnitude value from the first frequency row; and
include the range bin in the set of range bins.

9. The electronic device of claim 7, wherein the processor is further configured to:
combine a selected clutter removed CIR window, of the clutter removed CIR windows, with a mirrored copy of the selected clutter removed CIR window to generate a modified CIR window;
generate the power spectrum density from the modified CIR window;
identify the first set of signal components based on properties of the frequency spectrum; and
identify the second set of signal components based on the first set of signal components and properties of the power spectrum density.

10. The electronic device of claim 9, wherein to identify the heart rate, the processor is configured to:
identify a set of peaks of the power spectrum density, wherein the set of peaks includes breathing rate peaks, breathing harmonic peaks, heart rate peaks, and heart rate harmonic peaks;
remove one or more peaks that corresponds to the respiration rate from the set of peaks;
after removing the one or more peaks, identify a set of candidate heart rate peaks from the set of peaks that satisfy a set of predefined conditions; and
identify the heart rate from the set of candidate heart rate peaks based on properties of the set of candidate heart rate peaks including heart rate harmonics.

11. A method for contactless vital sign monitoring, the method comprising:
transmitting, via a transceiver, radar signals for object detection;
generating a clutter removed channel impulse response (CIR) from received reflections of the radar signals, a portion of which are reflected off of a living object;
identifying a set of range bins corresponding to a position of the living object based in part on the clutter removed CIR, wherein the portion of the clutter removed CIR includes a set of non-stationary signals that respectively correspond to each range bin among the set of range bins; and
identifying a first set of signal components representing a respiration rate of the living object and a second set of signal components representing a heart rate of the living object,
wherein identifying the first set of signal components and the second set of signal components comprises:
identifying the first set of signal components and the second set of signal components using variational mode decomposition (VMD) that decomposes each non-stationary signal of the set of non-stationary signals into subcomponents representing the respiration rate and the heart rate, or
identifying the first set of signal components from a generated frequency spectrum and identify the second set of signal components based on properties of a generated power spectrum density using the set of range bins; and
wherein using the VMD that decomposes each non-stationary signal into subcomponents representing the respiration rate and the heart rate further comprises:
decomposing, using VMD, a real part of each non-stationary signal into multiple narrow band components, wherein each of the narrow band components is centered around a respective frequency; and decomposing, using VMD, an imaginary part of each non-stationary signal into the multiple narrow band components centered around the respective frequencies.

12. The method of claim 11, wherein identifying the set of range bins corresponding to the position of the living object, comprises:

identifying standard deviation values for range bins of the clutter removed CIR; and comparing the standard deviation values corresponding to the range bins to identify one or more of the range bins based on a predefined criteria as the set of range bins corresponding to the position of the living object.

13. The method of claim 11, wherein identifying the set of range bins corresponding to the position of the living object, comprises:

identifying total energy values for range bins of the clutter removed CIR; and comparing the total energy values corresponding to the range bins to identify one or more of the range bins based on a predefined criteria as the set of range bins corresponding to the position of the living object.

14. The method of claim 11, wherein identifying the first set of signal components and the second set of signal components using VMD, the method comprises:

classifying the multiple narrow band components of the decomposed real and imaginary parts of each non-stationary signal of the set of non-stationary signals into different groups corresponding to different frequency ranges; and identifying the respiration rate and the heart rate based on properties of the different groups.

15. The method of claim 14, wherein:

the different groups include a breathing rate group, a respiration harmonics group, a heart rate group, and a heart rate harmonics group; and the method further comprises:

generating an output representing a final respiration rate based on a median value of the breathing rate group, and generating an output representing a final heart rate based on a median value of the heart rate group and a median value of a portion of the heart rate harmonics group.

16. The method of claim 11, wherein identifying the first set of signal components from the generated frequency spectrum and identifying the second set of signal components based on the properties of the generated power spectrum density using the set of range bins, the method comprises:

segmenting the clutter removed CIR into clutter removed CIR windows of a predefined size;

generating the frequency spectrum from the clutter removed CIR windows using a chirp-Z transform; and identifying the set of range bins based on properties of the frequency spectrum.

17. The method of claim 16, wherein identifying the set of range bins based on properties of the frequency spectrum and the respiration rate, comprises:

identifying, from the frequency spectrum, an average power of a set of continuous range bins for each frequency row of a plurality of frequency rows;

selecting a first frequency row from the plurality of frequency rows that includes a peak that satisfies a predefined criteria and includes a prominence greater than a threshold;

identifying the respiration rate based on a frequency value corresponding to the first frequency row;

identifying a range bin with a highest magnitude value from the first frequency row; and including the range bin in the set of range bins.

18. The method of claim 16, further comprising:

combining a selected clutter removed CIR window, of the clutter removed CIR windows, with a mirrored copy of the selected clutter removed CIR window to generate a modified CIR window;

generating the power spectrum density from the modified CIR window;

identifying the first set of signal components based on the properties of the frequency spectrum; and identifying the second set of signal components based on the first set of signal components and properties of the power spectrum density.

19. The method of claim 18, wherein identify the heart rate comprises:

identifying a set of peaks of the power spectrum density, wherein the set of peaks includes breathing rate peaks, breathing harmonic peaks, heart rate peaks, and heart rate harmonic peaks;

removing one or more peaks that corresponds to the respiration rate from the set of peaks;

after removing the one or more peaks, identify a set of candidate heart rate peaks from the set of peaks that satisfy a set of predefined conditions; and identifying the heart rate from the set of candidate heart rate peaks based on properties of the set of candidate heart rate peaks including heart rate harmonics.

20. A non-transitory computer-readable medium embodying a computer program, the computer program comprising computer readable program code that, when executed by a processor of an electronic device, causes the processor to:

transmit, via a transceiver, radar signals for object detection;

generate a clutter removed channel impulse response (CIR) from received reflections of the radar signals, a portion of which are reflected off of a living object;

identify a set of range bins corresponding to a position of the living object based in part on the clutter removed CIR, wherein the portion of the clutter removed CIR includes a set of non-stationary signals that respectively correspond to each range bin among the set of range bins; and identify a first set of signal components representing a respiration rate of the living object and a second set of signal components representing a heart rate of the living object;

wherein to identify the first set of signal components and the second set of signal components, the computer program further comprises computer readable program code that, when executed by the processor, causes the processor to:

identify the first set of signal components and the second set of signal components using variational mode decomposition (VMD) that decomposes each non-stationary signal of the set of non-stationary signals into subcomponents representing the respiration rate and the heart rate, or identify the first set of signal components from a generated frequency spectrum and identify the second set of signal components based on properties of a generated power spectrum density using the set of range bins; and wherein to use the VMD that decomposes each non-stationary signal into subcomponents representing the respiration rate and the heart rate, the computer program further comprises computer readable program code that, when executed by the processor, causes the processor to:
- decompose, using VMD, a real part of each non-stationary signal into multiple narrow band components, wherein each of the narrow band components is centered around a respective frequency; and
- decompose, using VMD, an imaginary part of each non-stationary signal into the multiple narrow band components centered around the respective frequencies.

* * * * *